US010718010B2

(12) United States Patent
Song et al.

(10) Patent No.: US 10,718,010 B2
(45) Date of Patent: Jul. 21, 2020

(54) NONINVASIVE DIAGNOSTICS BY SEQUENCING 5-HYDROXYMETHYLATED CELL-FREE DNA

(71) Applicant: The Board of Trustees of the Leland Stanford Junior University, Stanford, CA (US)

(72) Inventors: Chunxiao Song, Oxford (GB); Stephen R. Quake, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/146,807

(22) Filed: Sep. 28, 2018

(65) Prior Publication Data
US 2019/0017109 A1    Jan. 17, 2019

Related U.S. Application Data

(63) Continuation of application No. PCT/US2017/025735, filed on Apr. 3, 2017.

(60) Provisional application No. 62/319,702, filed on Apr. 7, 2016, provisional application No. 62/444,122, filed on Jan. 9, 2017, provisional application No. 62/461,712, filed on Feb. 21, 2017.

(51) Int. Cl.
| C12Q 1/68 | (2018.01) |
| C12Q 1/6855 | (2018.01) |
| C12Q 1/6869 | (2018.01) |
| C12Q 1/6806 | (2018.01) |
| C12Q 1/6886 | (2018.01) |
| C40B 40/08 | (2006.01) |
| C40B 50/04 | (2006.01) |
| C40B 70/00 | (2006.01) |

(52) U.S. Cl.
CPC ......... *C12Q 1/6855* (2013.01); *C12Q 1/6806* (2013.01); *C12Q 1/6869* (2013.01); *C12Q 1/6886* (2013.01); *C12Q 2525/191* (2013.01); *C12Q 2545/101* (2013.01); *C12Q 2563/185* (2013.01); *C12Q 2600/154* (2013.01); *C40B 40/08* (2013.01); *C40B 50/04* (2013.01); *C40B 70/00* (2013.01)

(58) Field of Classification Search
None
See application file for complete search history.

(56) References Cited

U.S. PATENT DOCUMENTS

| 8,741,567 B2 | 6/2014 | He et al. | |
| 9,816,986 B2 | 11/2017 | Rao et al. | |
| 2006/0281122 A1* | 12/2006 | Bryant | C12Q 1/6886 435/6.16 |
| 2010/0273151 A1 | 10/2010 | Tapscott et al. | |
| 2012/0034685 A1* | 2/2012 | Sparks | C12Q 1/6827 435/287.2 |
| 2012/0122087 A1* | 5/2012 | Li | C12Q 1/6886 435/6.11 |
| 2015/0011403 A1* | 1/2015 | Lo | C12O 1/6881 506/2 |
| 2015/0011408 A1 | 1/2015 | Kester | |
| 2015/0051113 A1* | 2/2015 | Kim | C12O 1/6806 506/16 |
| 2017/0253924 A1 | 9/2017 | Lu et al. | |
| 2018/0046754 A1* | 2/2018 | Batagov | G16B 20/00 |

FOREIGN PATENT DOCUMENTS

| WO | WO 2010114599 A1 | 10/2010 |
| WO | WO 2011025819 A1 | 3/2011 |
| WO | WO 2014/168711 | 10/2014 |
| WO | WO 2015/021282 | 2/2015 |

OTHER PUBLICATIONS

Fan et al. (Clinical Chemistry 2010 vol. 56 p. 1279) (Year: 2010).*
Zhou et al. (North American Journal of Medicine and.*
Castro et al., "5-Methylcytosine attack by hydroxyl free radicals and during carbon tetrachloride promoted liver microsomal lipid peroxidation: structure of reaction products", Chemico-Biological Interactions, 1996, 99:289-299.
Park et al., "Detection of DNA adducts by high-performance liquid chromatography with electrochemical detection", Carcinogenesis, 1989, 10(5): 827-832.
Song et al., "Specific Method for the Determination of Genomic DNA Methylation by Liquid Chromatography-Electrospray Ionization Tandem Mass Spectrometry", Anal. Chem., 2005, 77: 504-510.
Mellen et al., "MeCP2 binds to 5hmc enriched within active genes and accessible chromatin in the nervous system", Cell, 2012, 151(7): 1417-1430, doi:10.1016/j.cell.2012.11.022.
Song et al., "Selective chemical labeling reveals the genome-wide distribution of 5-hydroxymethylcytosine", Nat Biotechnol., 2011, 29(1): 68-72, doi:10.1038/nbt.1732.
Song et al., "Simultaneous single-molecule epigenetic imaging of DNA methylation and hydroxymethylation", Proceedings of the National Academy of Sciences, 2016, 113(16): 4338-4343.
Thomson et al., "Comparative analysis of affinity-based 5-hydroxymethylation enrichment techniques", Nucleic Acids Research, 2013, 41(22): e206, doi:10.1093/nar/gkt1080.
Wei et al., "Rapid Short-Read Sequencing and Aneuploidy Detection Using MinION Nanopore Technology", Genetics, 2015, 202(1): 37-44.

(Continued)

Primary Examiner — Katherine D Salmon
(74) Attorney, Agent, or Firm — James S. Keddie; Bozicevic, Field & Francis LLP

(57) ABSTRACT

Provided herein is a method of sequencing hydroxymethyated cell-free DNA. In some embodiments, the method comprises adding an affinity tag to only hydroxymethyated DNA molecules in a sample of cfDNA, enriching for the DNA molecules that are tagged with the affinity tag; and sequencing the enriched DNA molecules.

11 Claims, 14 Drawing Sheets

Specification includes a Sequence Listing.

(56) References Cited

OTHER PUBLICATIONS

Jin et al., "Chapter 6" in "Circulating Methylated DNA as Biomarkers for Cancer Detection", 2013, INTECH, XP055516486, pp. 137-152.
Globisch et al., "Tissue Distribution of 5-Hydroxymethylcytosine and Search for Active Demethylation Intermediates", PLoS ONE, 2010, 5(12): e15367.
Song et al., "5-Hydroxymethylcytosine signatures in cell-free DNA provide information about tumor types and stages", Cell Research, 2017, 27:1231-1242.

* cited by examiner

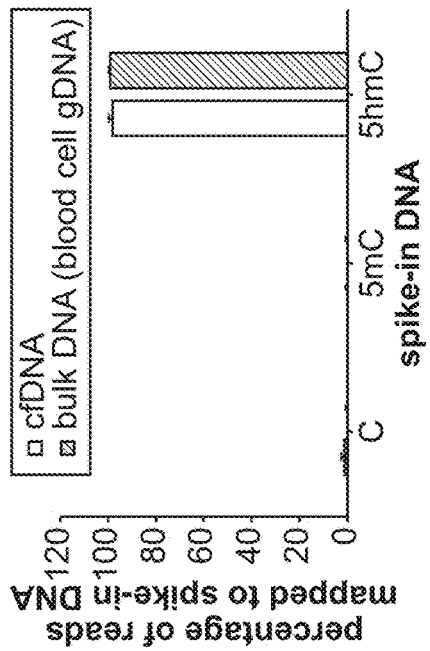
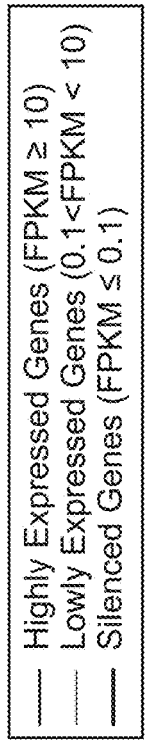
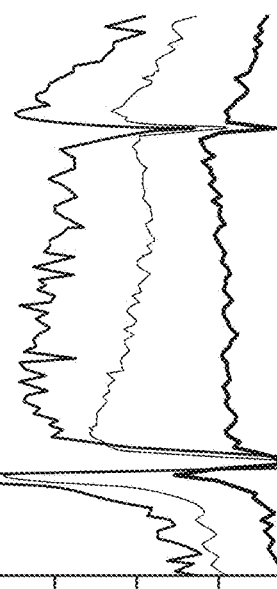
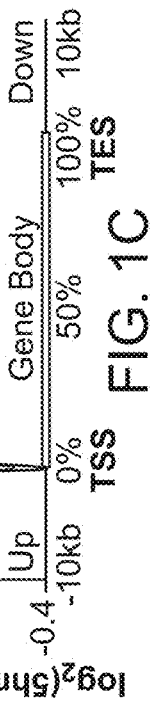
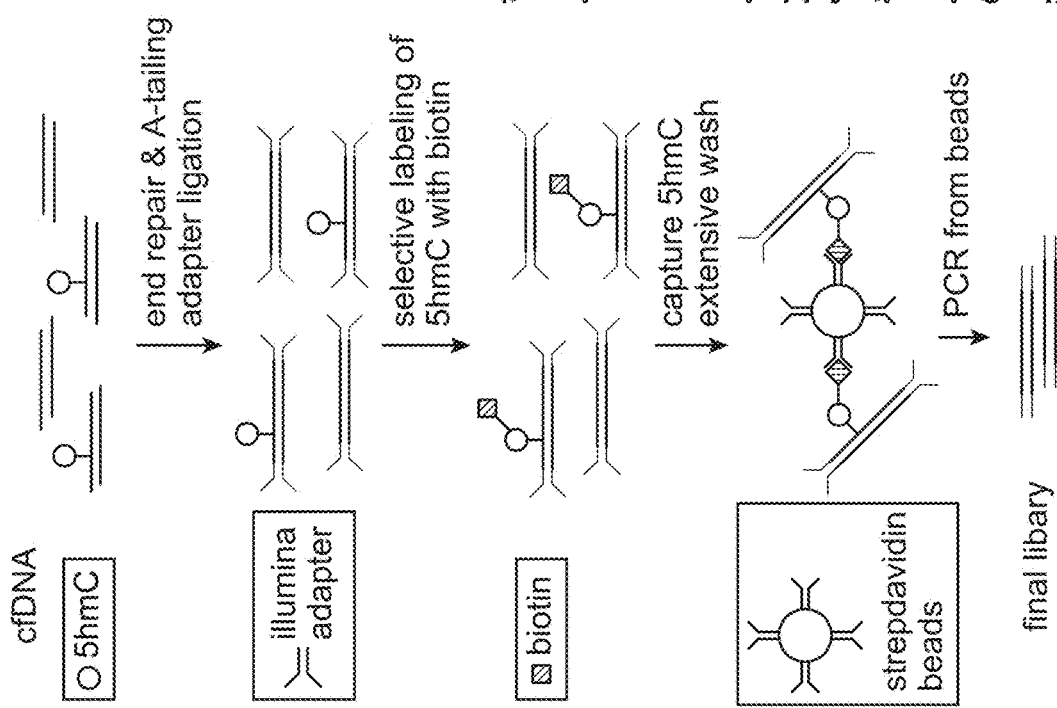
FIG. 1A
FIG. 1B
FIG. 1C

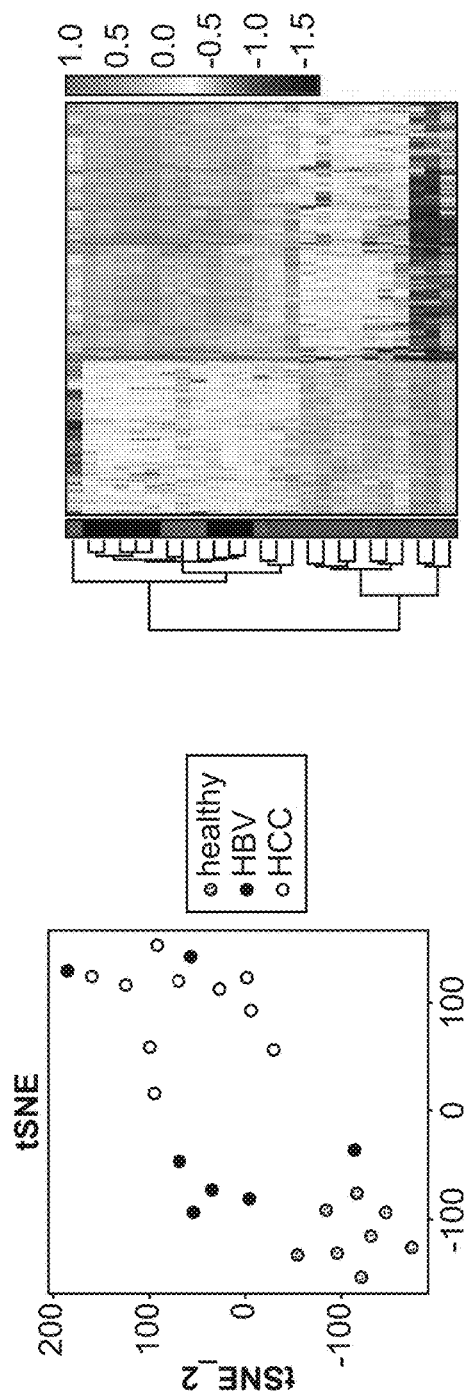
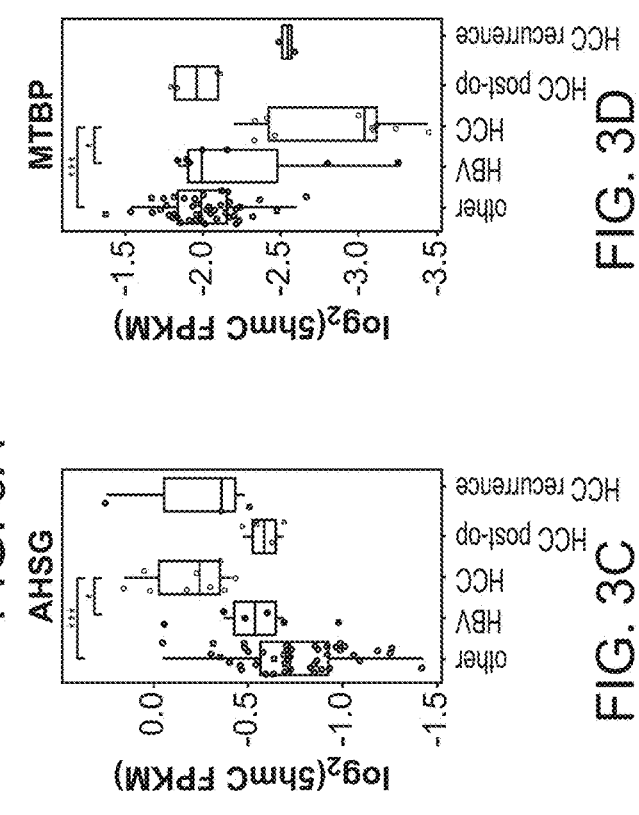
FIG. 3A, FIG. 3B, FIG. 3C, FIG. 3D, FIG. 3E

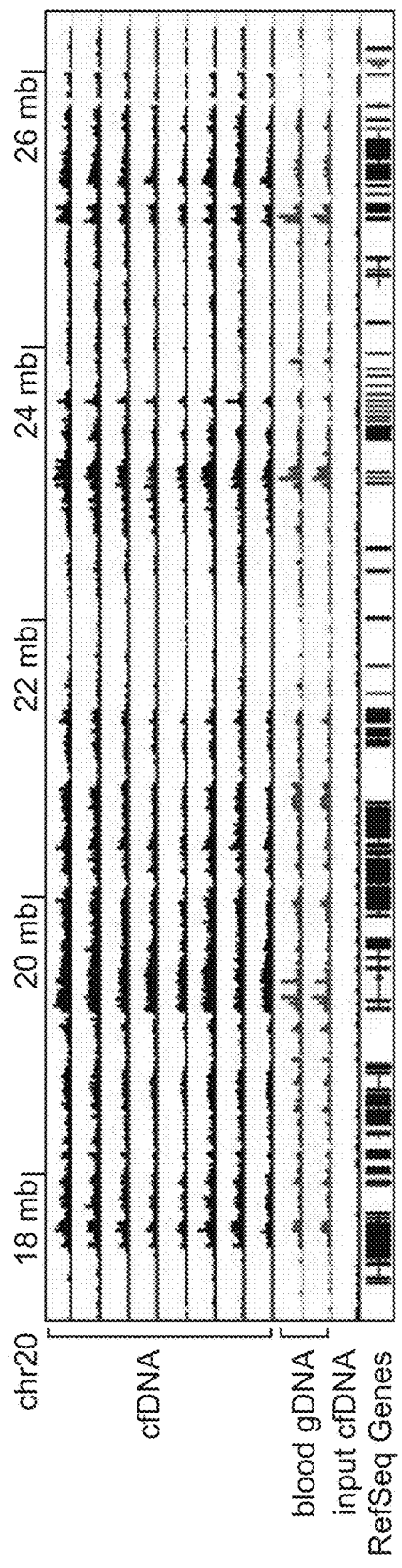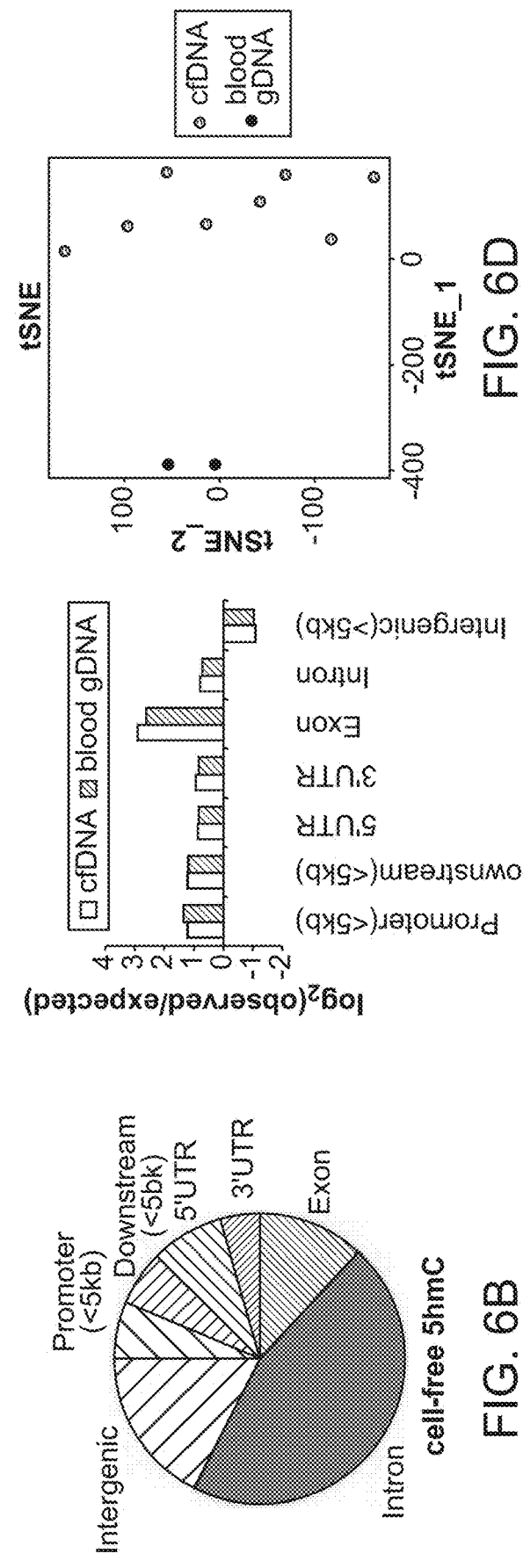
FIG. 6A
FIG. 6B
FIG. 6C
FIG. 6D

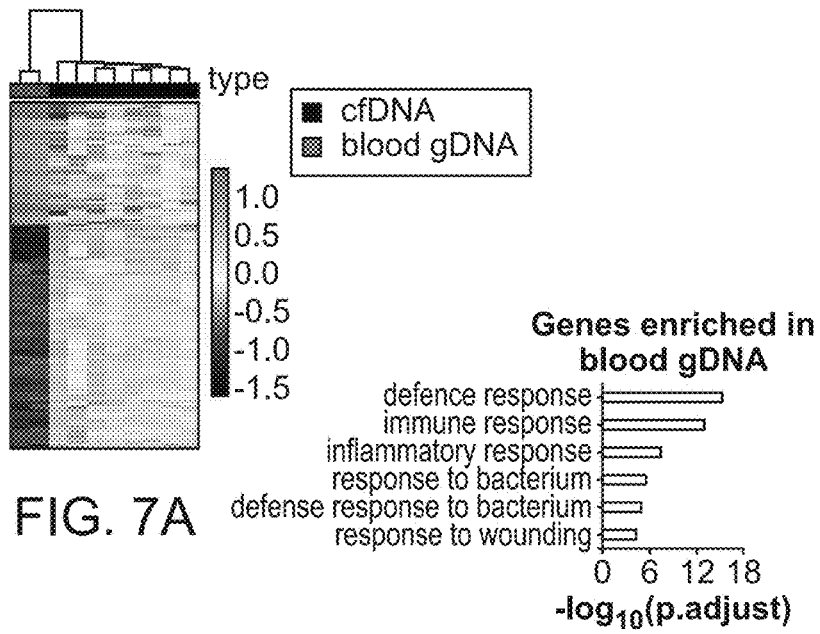
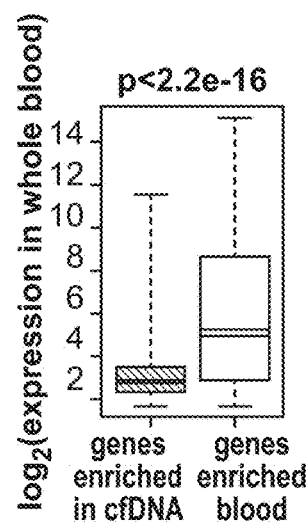
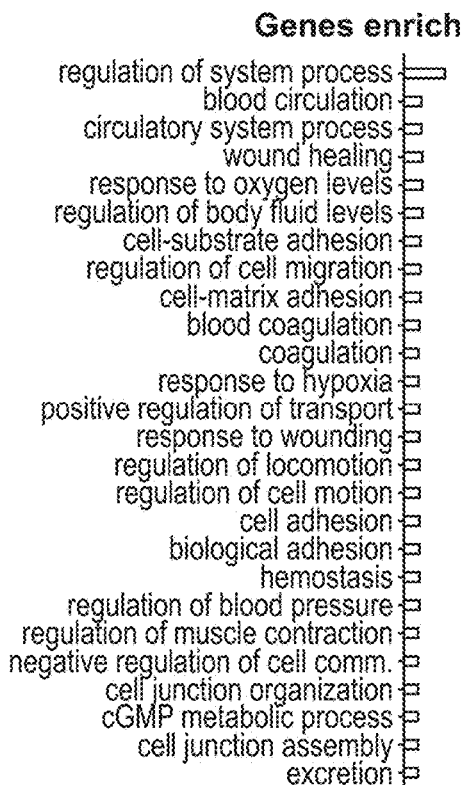
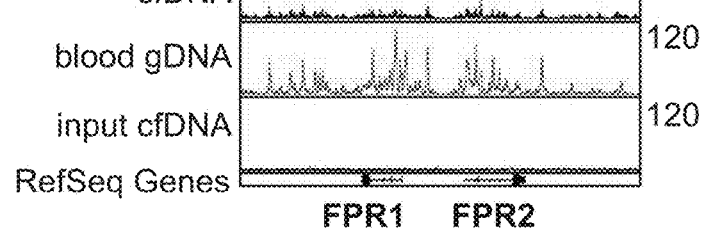
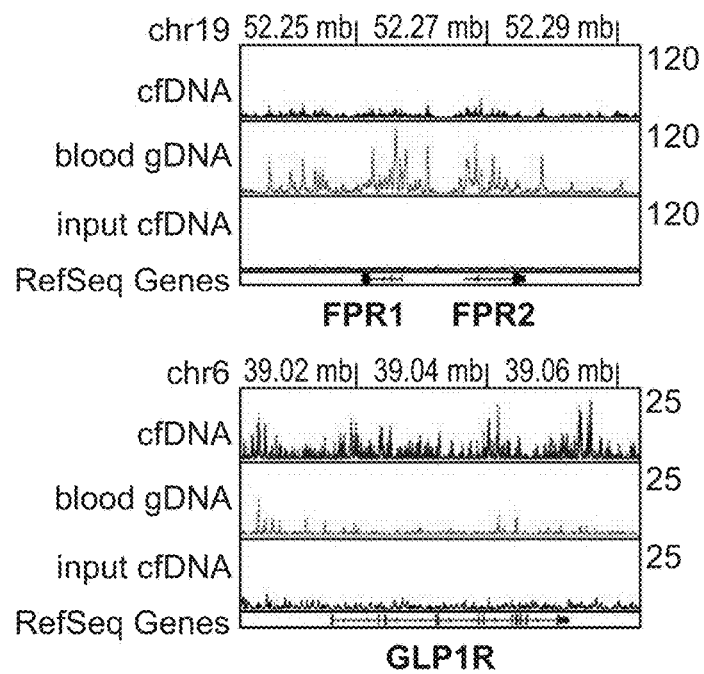
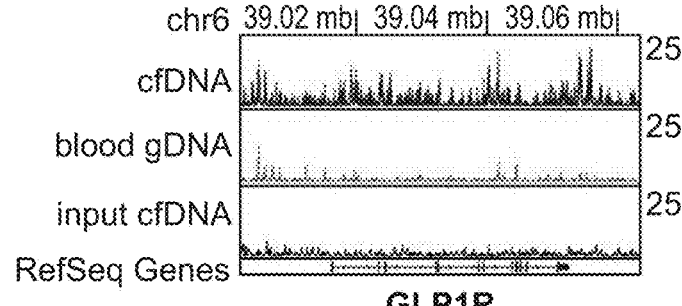

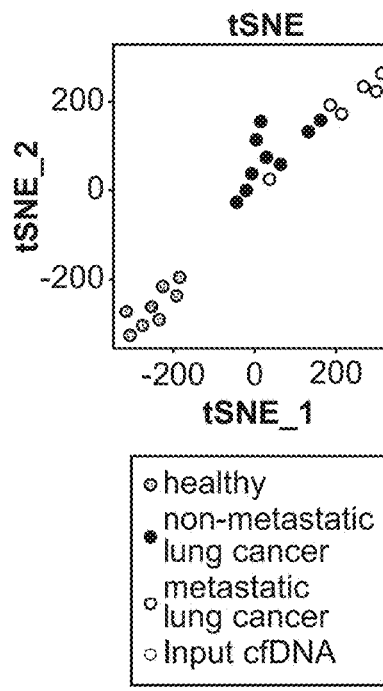
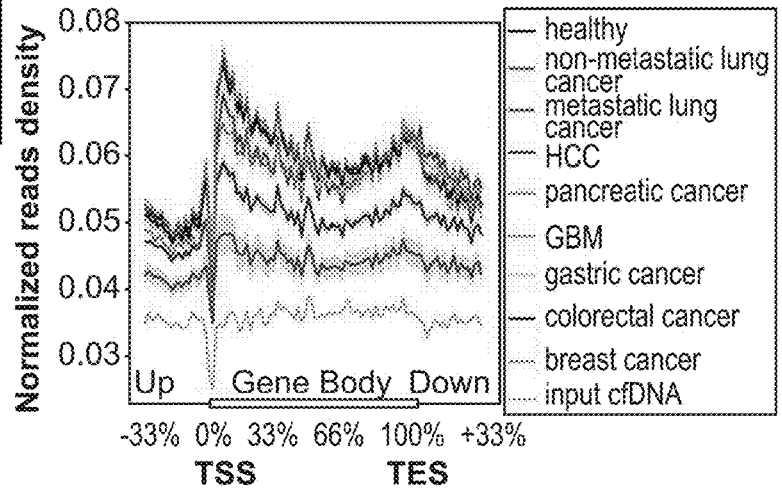
FIG. 8A
FIG. 8B
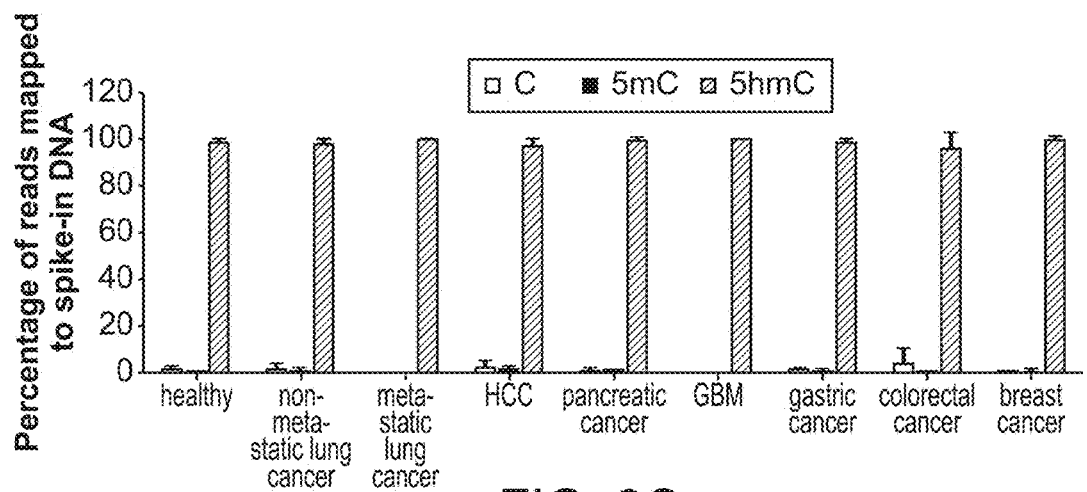
FIG. 8C
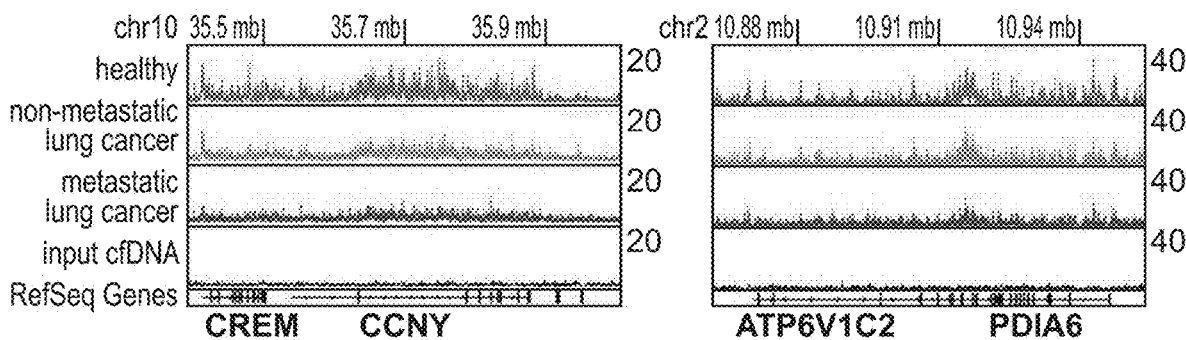
FIG. 8D

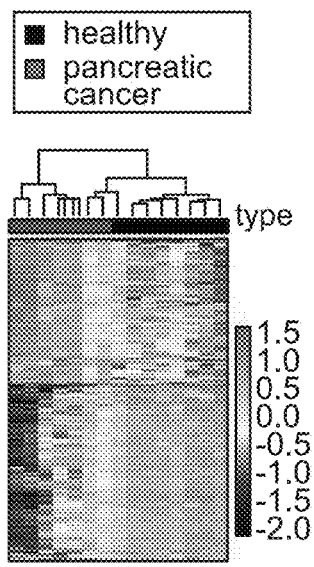
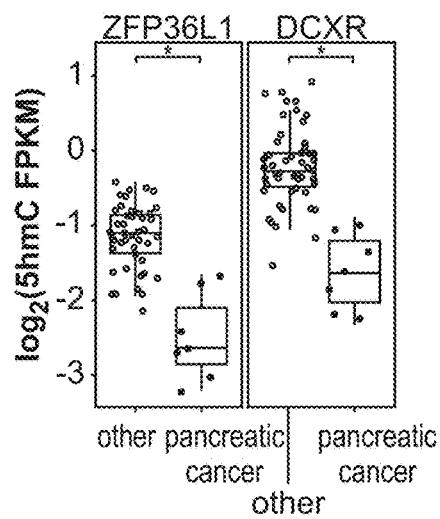
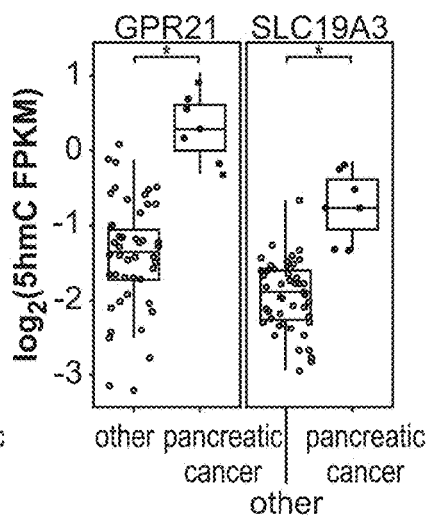
FIG. 10A  FIG. 10B  FIG. 10C
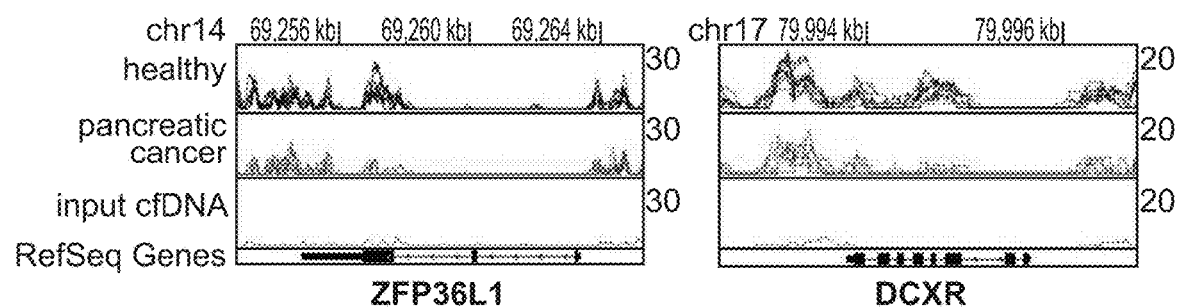
FIG. 10D
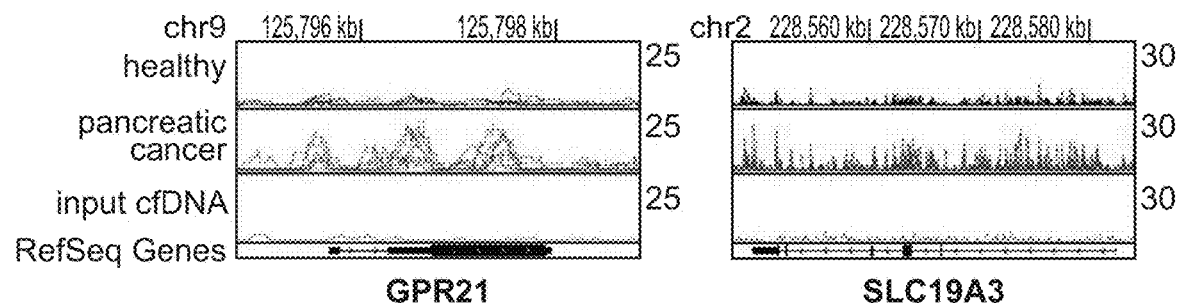
FIG. 10E

SEQUENCE LISTING

```
<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 1
cgtttccgtt cttcttcgtc                                                 20

<210> SEQ ID NO 2
```

```
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 2
tactcgcacc gaaaatgtca                                              20

<210> SEQ ID NO 3
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 3
gtggcgggtt atgatgaact                                              20

<210> SEQ ID NO 4
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 4
cataaaatgc ggggattcac                                              20

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
tgaaaacgaa aggggatacg                                              20

<210> SEQ ID NO 6
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
gtccagctgg gagtcgatac                                              20
```

NONINVASIVE DIAGNOSTICS BY SEQUENCING 5-HYDROXYMETHYLATED CELL-FREE DNA

CROSS-REFERENCING

This application is a continuation of International Application No. PCT/US2017/025735, filed on Apr. 3, 2017, which claims the benefit of U.S. provisional application Ser. No. 62/319,702, filed Apr. 7, 2016, 62/444,122, filed Jan. 9, 2017, and 62/461,712, filed Feb. 21, 2017, which applications are incorporated by reference in their entirety.

BACKGROUND

DNA modifications in the form of 5-methylcytosine (5mC) and the recently identified 5-hydroxymethylcytosine (5hmC) represent the two major epigenetic marks found in mammalian genome and they impact a broad range of biological processes from gene regulation to normal development. Detecting aberrant 5mC and 5hmC changes in the cell-free DNA (cfDNA) may represent an attractive noninvasive approach for cancer diagnostics. cfDNA is the circulating DNA found in our blood originated from different tissues and has been utilized for noninvasive prenatal tests, organ transplant diagnostics, and cancer detection. Compared to the intensive research on cell-free 5mC DNA as a biomarker for cancer diagnostics, cell-free 5hmC DNA has remain unexploited, mostly due to the low level of 5hmC compared to 5mC in the human genome (10 to 100-fold less than 5mC) and the lack of a sensitive low-input 5hmC DNA sequencing method to work with the minute amounts of cfDNA (typically only a few nanograms per ml of plasma).

SUMMARY

Provided herein, among other things, is a method of sequencing hydroxymethyated DNA in a sample of circulating cell-free DNA. In some embodiments, the method comprises adding an affinity tag to only hydroxymethyated DNA molecules in a sample of cfDNA, enriching for the DNA molecules that are tagged with the affinity tag; and sequencing the enriched DNA molecules.

In some embodiments, the method comprises: adding adaptor sequences onto the ends of the cfDNA; incubating the adaptor-ligated cfDNA with a DNA β-glucosyltransferase and UDP glucose modified with a chemoselective group, thereby covalently labeling the hyroxymethylated DNA molecules in the cfDNA with the chemoselective group; linking a biotin moiety to the chemoselectively-modified cfDNA via a cycloaddition reaction; enriching for biotinylated DNA molecules by binding to a support that binds to biotin; amplifying the enriched DNA using primers that bind to the adaptors; and sequencing the amplified DNA to produce a plurality of sequence reads.

A method comprising: (a) obtaining a sample comprising circulating cell-free DNA, (b) enriching for the hydroxymethylated DNA in the sample, and (c) independently quantifying the amount of nucleic acids in the enriched hydroxymethylated DNA that map to each of one or more target loci is also provided.

Among other things, the sequences obtained from the method can be used as a diagnostic, theranostic or prognostic for a variety of diseases or conditions, for example.

Also provided are a variety of compositions, including a composition comprising circulating cell-free DNA, wherein the hydroxymethylcytosines residues in the DNA are modified to contain a capture tag.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way FIGS. 1A-1C: Sequencing of 5hmC in cfDNA. FIG. 1A: General procedure of cell-free 5hmC sequencing. cfDNA is ligated with Illumina adapter and labeled with biotin on 5hmC for pull-down with streptavidin beads. The final library is completed by directly PCR from streptavidin beads. FIG. 1B: Percentage of reads mapped to spike-in DNA in the sequencing libraries. Error bars indicate s.d. FIG. 1C: Metagene profiles of log 2 fold change of cell-free 5hmC to input cfDNA ratio in genes ranked according to their expression in cell-free RNA-Seq.

FIG. 2A: Genome browser view of the cell-free 5hmC distribution in a 10 mb region in chromosome 6. Showing the overlap tracks of healthy, non-metastatic lung cancer, metastatic lung cancer, and input cfDNA samples in line plot. FIG. 2B: Heatmap of 1,159 metastatic lung cancer differential genes in healthy, lung cancer samples and the unenriched input cfDNA. Hierarchical clustering was performed across genes and samples. FIG. 2C: Boxplot of number of hMRs (normalized to 1 million reads) identified in each group. FIG. 2D: Boxplots of CCNY and PDIA6 5hmC FPKM in lung cancer and other cfDNA samples. *P<0.05, P<0.01, *P<0.001, ****P<1e-5, Welch t-test.

FIGS. 3A-3E: Cell-free 5hmC for monitoring HCC progression and treatment. FIG. 3A: tSNE plot of 5hmC FPKM from healthy, HBV and HCC samples. FIG. 3B: Heatmap of 1,006 HCC differential genes in healthy, HBV and HCC samples. Hierarchical clustering was performed across genes and samples. FIGS. 3C-3D: Boxplots of AHSG (FIG. 3C) and MTBP (FIG. 3D) ShmC FPKM in HBV, HCC (pre-op), HCC post-op, HCC recurrence and other cfDNA samples. *P<0.05, P<1e-4, *P<1e-5, Welch t-test. FIG. 3E: tSNE plot of ShmC FPKM from healthy, HCC pre-op, HCC post-op and HCC recurrence samples.

FIG. 4A: tSNE plot of ShmC FPKM in cfDNA from healthy and various cancer samples. FIG. 4B: The actual and predicted classification by leave-one-out cross-validation using Mclust (MC) and Random Forest (RF) algorithm, based on two feature sets (gene body and DhMR). FIG. 4C: The Cohen's kappa coefficient for measuring inter-classifier agreement (GB for gene body). The error bar indicates the standard error of the Cohen's kappa estimate.

FIG. 5A: hMe-Seal reactions. ShmC in DNA is labeled with an azide-modified glucose by βGT, which is then linked to a biotin group through click chemistry. FIG. 5B: Enrichment tests of a single pool of amplicons containing C, 5mC or ShmC spiked into cfDNA. Showing gel analysis that after hMe-Seal, only ShmC-containing amplicon can be PCRed from the streptavidin beads. FIG. 5C: Boxplot of sequencing depth across all cell-free samples. FIG. 5D: Boxplot of unique nonduplicate map rate across all cell-free samples. FIG. 5E: MA-plot of normalized cell-free ShmC read counts (reads/million) in 10 kb bins genome-wide between technical duplicate. The horizontal blue line M=0 indicates same value in two sample. A lowess fit (in red) is plotted underlying a possible trend in the bias related to the mean value. FIG. 5F: Venn diagram of hMRs overlap between technical replications of cell-free ShmC sequencing and a pooled sample from both replicates.

FIGS. 6A-6D: Genome-wide distribution of ShmC in cfDNA. FIG. 6A: Genome browser view of the ShmC distribution in a 10 mb region in chromosome 20. Showing the tracks of enriched cfDNA and whole blood gDNA samples along with the unenriched input cfDNA. FIG. 6B: Pie chart presentation of the overall genomic distribution of hMRs in cfDNA. FIG. 6C: The relative enrichment of hMRs across distinct genomic regions in cfDNA and whole blood gDNA. FIG. 6D: tSNE plot of ShmC FPKM in cfDNA and whole blood gDNA from healthy samples.

FIGS. 7A-7E: Differential 5hmC signals between cfDNA and whole blood gDNA. FIG. 7A: Heatmap of 2,082 differential genes between cfDNA and blood gDNA. Hierarchical clustering was performed across genes and samples. FIG. 7B: Boxplot of expression level in whole blood for cfDNA and whole blood gDNA 5hmC enriched genes. The p-value is shown on top. FIGS. 7C and 7D: GO analysis of the whole blood-specific (FIG. 7C) and cfDNA-specific (FIG. 7D) 5hmC enriched genes, adjusted p-value cut off 0.001. FIG. 7E: Genome browser view of the 5hmC distribution in the FPR1/FPR2 (top) and the GLP1R (bottom) loci. Showing the overlap tracks of cfDNA, whole blood gDNA and input cfDNA in line plot.

FIGS. 8A-8D: Cell-free hydroxymethylome in lung cancer. FIG. 8A: tSNE plot of 5hmC FPKM from healthy, non-metastatic lung cancer and metastatic lung cancer samples, along with the unenriched input cfDNA. FIG. 8B: Metagene profiles of cell-free 5hmC in healthy and various cancer groups, along with unenriched input cfDNA. Shaded area indicate s.e.m. FIG. 8C: Percentage of reads mapped to spike-in DNA in the sequencing libraries of various groups. Error bars indicate s.d. FIG. 8D: Genome browser view of the cell-free 5hmC distribution in the CREM/CCNY (left) and ATP6V1C2/PDIA6 (right) loci in healthy and lung cancer samples. Showing the overlap tracks in line plot.

FIG. 9A: Boxplot of expression level in liver tissue for HCC-specific 5hmC enriched and depleted genes. The p-value is shown on top. FIG. 9B: Genome browser view of the cell-free 5hmC distribution in the AHSG locus in healthy HBV and HCC samples. Showing the overlap tracks in line plot. FIG. 9C: Expression of AHSG in liver and other tissues. FIG. 9D: Genome browser view of the cell-free 5hmC distribution in the MTBP locus in healthy, HBV and HCC samples. Showing the overlap tracks in line plot. FIG. 9E: Changes of HCC score in 4 HCC follow-up cases. Disease status shown on the bottom. Time duration in month shown on the top. Dotted lines indicate the median values of HCC scores in the HCC, HBV, and healthy groups. Triangles indicate treatment. HCC score is a linear combination of 1,006 HCC differential genes (FIG. 3B) that best separates HCC from HBV and healthy samples.

FIGS. 10A-10E: Cell-free hydroxymethylome in pancreatic cancer. FIG. 10A: Heatmap of 713 pancreatic cancer differential genes in healthy and pancreatic cancer samples. Hierarchical clustering was performed across genes and samples. FIGS. 10B and 10C, Boxplots of ZFP36L1, DCXR (FIG. 10B) and GPR21, SLC19A3 (FIG. 10C) 5hmC FPKM in pancreatic cancer and other cfDNA samples. *P<0.001, P<1e-5, Welch t-test. FIGS. 10D and 10E: Genome browser view of the cell-free 5hmC distribution in the ZFP36L1, DCXR (FIG. 10D) and GPR21, SLC19A3 (FIG. 10E**) loci in healthy and pancreatic cancer samples. Showing the overlap tracks in line plot.

FIG. 11A: tSNE plot of promoters 5hmC FPKM (5 kb upstream of TSS) from healthy and various caner samples. FIG. 11B: tSNE plot of 5hmC FPKM from healthy and various caner cfDNA samples along with the whole blood gDNA samples. FIG. 11C: Age distribution of healthy individual and various cancer patients. FIG. 11D: tSNE plot of 5hmC FPKM in cfDNA from healthy and various cancer samples (FIG. 4A) colored by batches numbered according to the process time.

FIGS. 12A and 12B: Bayesian Information Criterion (BIC) plot by Mclust trained with 90 gene body feature set (FIG. 12A) and 17 DhMRs feature set (FIG. 12B), indicating high BIC value for separating five groups when using EEI model for Mclust. FIG. 12C, 4-Dimensional Mclust-based dimensionality reduction plot using DhMRs features. The lower half shows the scatter plot and the upper half shows the density plot. FIGS. 12D and 12E: Variable importance (mean decrease Gini) for the top 15 gene bodies (FIG. 12D) and DhMRs (FIG. 12E), in the random forest training model. FIGS. 12F and 12G show the variable importance for gene bodies and DhMRS, obtained using a different method.

DEFINITIONS

Figure 2A:
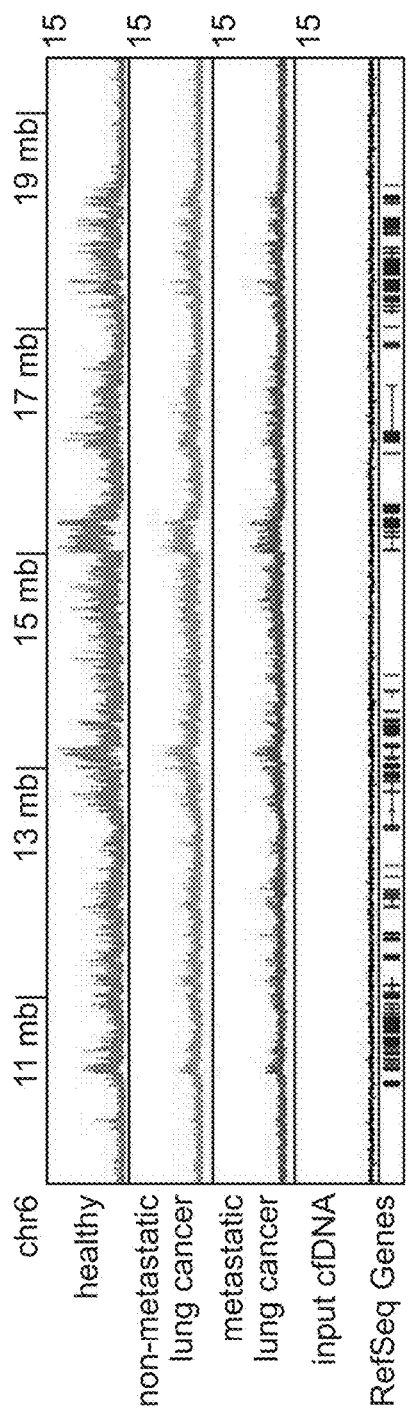
FIGS. 2A-2D: Lung cancer leads to progressive loss of 5hmC enrichment in cfDNA.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest.

The term "nucleic acid sample," as used herein denotes a sample containing nucleic acids. Nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein. A nucleic acid sample can be made from any suitable source, including a sample of tooth, bone, hair or bone, etc.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA. Also included in this definition are ZNAs, i.e., zip nucleic acids.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "ligating," as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary," each base of one of the nucleic acids base pairs with corresponding nucleotides in the other nucleic acid. Two nucleic acids do not need to be perfectly complementary in order to hybridize to one another.

The term "separating," as used herein, refers to physical separation of two elements (e.g., by size or affinity, etc.) as well as degradation of one element, leaving the other intact.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences. The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

The term "adaptor" refers to a nucleic acid that is ligatable to both strands of a double-stranded DNA molecule. In one embodiment, an adaptor may be a hairpin adaptor (i.e., one molecule that base pairs with itself to form a structure that has a double-stranded stem and a loop, where the 3' and 5' ends of the molecule ligate to the 5' and 3' ends of the double-stranded DNA molecule, respectively). In another embodiment, an adaptor may be a Y-adaptor. In another embodiment, an adaptor may itself be composed of two distinct oligonucleotide molecules that are base paired with one another. As would be apparent, a ligatable end of an adaptor may be designed to be compatible with overhangs made by cleavage by a restriction enzyme, or it may have blunt ends or a 5' T overhang. The term "adaptor" refers to double-stranded as well as single-stranded molecules. An adaptor can be DNA or RNA, or a mixture of the two. An adaptor containing RNA may be cleavable by RNase treatment or by alkaline hydrolysis. An adaptor may be 15 to 100 bases, e.g., 50 to 70 bases, although adaptors outside of this range are envisioned.

The term "adaptor-ligated," as used herein, refers to a nucleic acid that has been ligated to an adaptor. The adaptor can be ligated to a 5' end and/or a 3' end of a nucleic acid molecule.

The term "asymmetric adaptor", as used herein, refers to an adaptor that, when ligated to both ends of a double stranded nucleic acid fragment, will lead to a top strand that contains a 5' tag sequence that is not the same as or complementary to the tag sequence at the 3' end. Exemplary asymmetric adapters are described in: U.S. Pat. Nos. 5,712,126 and 6,372,434 and WO/2009/032167; all of which are incorporated by reference herein in their entirety. An asymmetrically tagged fragment can be amplified by two primers: one that hybridizes to a first tag sequence added to the 3' end of a strand, and another that hybridizes to the complement of a second tag sequence added to the 5' end of a strand. Y-adaptors and hairpin adaptors (which can be cleaved, after ligation, to produce a "Y-adaptor") are examples of asymmetric adaptors.

The term "Y-adaptor" refers to an adaptor that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adaptor-tagged double-stranded DNA that has been ligated to a Y-adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

The term "hairpin adaptor" refers to an adaptor that is in the form of a hairpin. In one embodiment, after ligation the hairpin loop can be cleaved to produce strands that have non-complementary tags on the ends. In some cases, the loop of a hairpin adaptor may contain a uracil residue, and the loop can be cleaved using uracil DNA glycosylase and endonuclease VIII, although other methods are known.

The term "adaptor-ligated sample", as used herein, refers to a sample that has been ligated to an adaptor. As would be understood given the definitions above, a sample that has been ligated to an asymmetric adaptor contains strands that have non-complementary sequences at the 5' and 3' ends.

An "oligonucleotide binding site" refers to a site to which an oligonucleotide hybridizes in a target polynucleotide. If an oligonucleotide "provides" a binding site for a primer, then the primer may hybridize to that oligonucleotide or its complement. The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "tagging" as used herein, refers to the appending of a sequence tag (that contains an identifier sequence) onto a nucleic acid molecule. A sequence tag may be added to the 5' end, the 3' end, or both ends of nucleic acid molecule. A sequence tag can be added to a fragment by ligating an adaptor to the fragment by, e.g., T4 DNA ligase or another ligase.

The term "molecular barcode" encompasses both sample identifier sequences and molecule identifier sequences, as described below. In some embodiments, a molecular barcode may have a length in range of from 1 to 36 nucleotides, e.g., from 6 to 30 nucleotides, or 8 to 20 nucleotides. In certain cases, the molecular identifier sequence may be error-correcting, meaning that even if there is an error (e.g., if the sequence of the molecular barcode is mis-synthesized, mis-read or is distorted by virtue of the various processing steps leading up to the determination of the molecular barcode sequence) then the code can still be interpreted correctly. Descriptions of exemplary error correcting sequences can be found throughout the literature (e.g., US20100323348 and US20090105959, which are both incorporated herein by reference). In some embodiments, an identifier sequence may be of relatively low complexity (e.g., may be composed of a mixture of 4 to 1024 different sequences), although higher complexity identifier sequences can be used in some cases.

The term "sample identifier sequence" and "sample index" is a sequence of nucleotides that is appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide. When elements of the sample identifier has sequence at each end, together, the 3' and 5' sample identifier sequences identify the sample. In many examples, the sample identifier sequence is only a subset of the bases which are appended to a target oligonucleotide.

The term "molecule identifier sequence" is a sequence of nucleotides that can be appended to the nucleic acid fragments of a sample such that the appended sequence of nucleotides, alone or in combination with other features of the fragments, e.g., their fragmentation breakpoints, can be used to distinguish between the different fragment molecules in the sample or a portion thereof. The complexity of a population of molecule identifier sequences used in any one implementation may vary depending on a variety of parameters, e.g., the number of fragments in a sample and/or the amount of the sample that is used in a subsequent step. For example, in certain cases, the molecule identifier sequence may be of low complexity (e.g., may be composed of a mixture of 8 to 1024 sequences). In other cases, the molecule identifier sequence may be of high complexity (e.g., may be composed of 1025 to 1M or more sequences). In certain embodiments, a population of molecule identifier sequences may comprise a degenerate base region (DBR) comprising one or more (e.g., at least 2, at least 3, at least 4, at least 5, or 5 to 30 or more) nucleotides selected from R, Y, S, W, K, M, B, D, H, V, N (as defined by the IUPAC code), or a variant thereof. As described in U.S. Pat. No. 8,741,606, a molecule identifier sequence may be made up of sequences that are non-adjacent. In some embodiments, a population of molecule identifier sequences may by made by mixing oligonucleotides of a defined sequence together. In these embodiments, the molecule identifier sequence in each of the oligonucleotides may be error correcting. In the methods described herein, the molecule identifier sequence may be used to distinguish between the different fragments in a portion of an initial sample, where the portion has been removed from the initial sample. The molecule identifier sequences may be used in conjunction with other features of the fragments (e.g., the end sequences of the fragments, which define the breakpoints) to distinguish between the fragments.

As used herein, the term "correspond to", with reference to a sequence read that corresponds to a particular (e.g., the top or bottom) strand of a fragment, refers to a sequence read derived from that strand or an amplification product thereof.

The term "covalently linking" refers to the production of a covalent linkage between two separate molecules.

As used herein, the term "circulating cell-free DNA" refers to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cfDNA can be highly fragmented and in some cases can have a mean fragment size about 165-250 bp (Newman et al Nat Med. 2014 20: 548-54). cfDNA can be obtained by centrifuging whole blood to remove all cells, and then isolating the DNA from the remaining plasma or serum. Such methods are well known (see, e.g., Lo et al, Am J Hum Genet 1998; 62:768-75). Circulating cell-free DNA is double-stranded, but can be made single stranded by denaturation.

As used herein, the term "adding adaptor sequences" refers to the act of adding an adaptor sequence to the end of fragments in a sample. This may be done by filling in the ends of the fragments using a polymerase, adding an A tail, and then ligating an adaptor comprising a T overhang onto the A-tailed fragments.

As used herein, the term "UDP glucose modified with a chemoselective group" refers to a UDP glucose that has been functionalized, particularly at the 6-hydroxyl position, to include a group that is capable of participating in a 1,3 cycloaddition (or "click") reaction. Such groups include azido and alkynyl (e.g., cyclooctyne) groups, although others are known (Kolb et al., 2001; Speers and Cravatt, 2004; Sletten and Bertozzi, 2009). UDP-6-$N_3$-Glu is an example of a UDP glucose modified with a chemoselective group, although others are known.

As used herein, the term "biotin moiety" refers to an affinity tag that includes biotin or a biotin analogue such as desthiobiotin, oxybiotin, 2-iminobiotin, diaminobiotin, biotin sulfoxide, biocytin, etc. Biotin moieties bind to streptavidin with an affinity of at least $10^{-8}$ M.

As used herein, the terms "cycloaddition reaction" and "click reaction" are described interchangeably to refer to a 1,3-cycloaddition between an azide and alkyne to form a five membered heterocycle. In some embodiments, the alkyne may be strained (e.g., in a ring such as cyclooctyne) and the cycloaddition reaction may done in copper free conditions. Dibenzocyclooctyne (DBCO) and difluorooctyne (DIFO) are examples of alkynes that can participate in a copper-free cycloaddition reaction, although other groups are known. See, e.g., Kolb et al (Drug Discov Today 2003 8 : 1128-113), Baskin et al (Proc. Natl. Acad. Sci. 2007 104: 16793-16797) and Sletten et al (Accounts of Chemical Research 2011 44: 666-676) for a review of this chemistry.

As used herein, the term "support that binds to biotin" refers to a support (e.g., beads, which may be magnetic) that is linked to streptavidin or avidin, or a functional equivalent thereof.

The term "amplifying" as used herein refers to generating one or more copies of a target nucleic acid, using the target nucleic acid as a template.

The term "copies of fragments" refers to the product of amplification, where a copy of a fragment can be a reverse complement of a strand of a fragment, or have the same sequence as a strand of a fragment.

The terms "enrich" and "enrichment" refers to a partial purification of analytes that have a certain feature (e.g., nucleic acids that contain hydroxymethylcytosine) from analytes that do not have the feature (e.g., nucleic acids that contain hydroxymethylcytosine). Enrichment typically increases the concentration of the analytes that have the feature (e.g., nucleic acids that contain hydroxymethylcytosine) by at least 2-fold, at least 5-fold or at least 10-fold relative to the analytes that do not have the feature. After enrichment, at least 10%, at least 20%, at least 50%, at least 80% or at least 90% of the analytes in a sample may have the feature used for enrichment. For example, at least 10%, at least 20%, at least 50%, at least 80% or at least 90% of the nucleic acid molecules in an enriched composition may contain a strand having one or more hydroxymethylcytosines that have been modified to contain a capture tag.

Other definitions of terms may appear throughout the specification.

DESCRIPTION OF EXEMPLARY EMBODIMENTS

Provided herein is a method of sequencing hydroxymethyated cell-free DNA. In some embodiments, the method comprises adding an affinity tag to only hydroxymethyated DNA molecules in a sample of cfDNA, enriching for the DNA molecules that are tagged with the affinity tag; and sequencing the enriched DNA molecules.

FIG. 1A shows one implementation of the method. In certain embodiments and with reference to FIG. 1A, the method may comprise: (a) adding adaptor sequences onto the ends of cell-free (cfDNA), (b) incubating the adaptor-ligated cfDNA with a DNA β-glucosyltransferase and UDP glucose modified with a chemoselective group, thereby covalently labeling the hyroxymethylated DNA molecules in the cfDNA with the chemoselective group; (c) linking a biotin moiety to the chemoselectively-modified cfDNA via a cycloaddition reaction; (d) enriching for the biotinylated DNA molecules by binding the product of the biotin labeling step (step c) to a support that binds to biotin; (e) amplifying the enriched DNA using primers that bind to the adaptors; and (f) sequencing the amplified DNA to produce a plurality of sequence reads.

As shown in FIG. 1A, in some embodiments, the method does not comprise releasing the biotinylated DNA molecules from the support prior to amplification (i.e., after step (d), prior to step (e)) and, as such, in some embodiments the amplifying step (d) may comprise amplifying the enriched DNA while it is bound to the support of (c). This may be implemented by: i. washing the support of (d) after the biotinylated DNA molecules have bound to the support; and then ii. setting up an amplification reaction containing the support, without releasing the biotinylated DNA molecules from the support.

Also as shown in FIG. 1A, step (a) may be implemented by ligating the DNA is to a universal adaptor, i.e., an adaptor that ligates to both ends of the fragments of cfDNA. In certain cases, the universal adaptor may be done by ligating a Y adaptor (or hairpin adaptor) onto the ends of the cfDNA, thereby producing a double stranded DNA molecule that has a top strand that contains a 5' tag sequence that is not the same as or complementary to the tag sequence added the 3' end of the strand. As should be apparent, the DNA fragments used in the initial step of the method should be non-amplified DNA that has not been denatured beforehand. As shown in FIG. 1A, this step may require polishing (i.e., blunting) the ends of the cfDNA with a polymerase, A-tailing the fragments using, e.g., Taq polymerase, and ligating a T-tailed Y adaptor to the A-tailed fragments. This initial ligation step may be done on a limiting amount of cfDNA. For example, cfDNA to which the adaptors are ligated may contain less than 200 ng of DNA, e.g., 10 pg to 200 ng, 100 pg to 200 ng, 1 ng to 200 ng or 5 ng to 50 ng, or less than 10,000 (e.g., less than 5,000, less than 1,000, less than 500, less than 100 or less than 10) haploid genome equivalents, depending on the genome. In some embodiments, the method is done using less than 50 ng of cfDNA (which roughly corresponds to approximately 5 mls of plasma) or less than 10 ng of cfDNA, which roughly corresponds to approximately 1 mls of plasma. For example, Newman et al (Nat Med. 2014 20: 548-54) made libraries from 7-32 ng cfDNA isolated from 1-5 mL plasma. This is equivalent to 2,121-9,697 haploid genomes (assuming 3.3 pg per haploid genome). The adaptor ligated onto the cfDNA may contain a molecular barcode to facilitate multiplexing and quantitative analysis of the sequenced molecules. Specifically, the adaptor may be "indexed" in that it contains a molecular barcode that identifies the sample to which it was ligated (which allows samples to be pooled before sequencing). Alternatively or in addition, the adaptor may contain a random barcode or the like. Such an adaptor can be ligated to the fragments and substantially every fragment corresponding to a particular region are tagged with a different sequence. This allows for identification of PCR duplicates and allows molecules to be counted.

In the next step of this implementation of the method, the hydroxymethylated DNA molecules in the cfDNA are labeled with a with the chemoselective group, i.e., a group that can participate in a click reaction. This step may be done by incubating the adaptor-ligated cfDNA with DNA β-glucosyltransferase (e.g., T4 DNA β-glucosyltransferase (which is commercially available from a number of vendors), although other DNA β-glucosyltransferases exist) and, e.g., UDP-6-$N_3$-Glu (i.e., UDP glucose containing an azide). This step may be done using a protocol adapted from US20110301045 or Song et al, (Nat. Biotechnol. 2011 29: 68-72), for example.

The next step of this implementation of the method involves adding a biotin moiety to the chemoselectively modified DNA via a cycloaddition (click) reaction. This step may be done by directly adding a biotinylated reactant, e.g., a dibenzocyclooctyne-modified biotin to the glucosyltransferase reaction after that reaction has been completed, i.e., after an appropriate amount of time (e.g., after 30 minutes or more). In some embodiments, the biotinylated reactant may be of the general formula B-L-X, where B is a biotin moiety, L is a linker and X is a group that reacts with the chemoselective group added to the cfDNA via a cycloaddition reaction. In certain cases, the linker may make the compound more soluble in an aqueous environment and, as such, may contain a polyethyleneglycol (PEG) linker or an equivalent thereof. In some embodiments, the added compound may be dibenzocyclooctyne-$PEG_n$-biotin, where N is 2-10, e.g., 4. Dibenzocyclooctyne-PEG4-biotin is relatively hydrophilic and is soluble in aqueous buffer up to a concentration of 0.35 mM. The compound added in this step does not need to contain a cleavable linkage, e.g., does not contain a disulfide linkage or the like. In this step, the cycloaddition reaction may be between an azido group added to the hydroxymethylated cfDNA and an alkynyl group (e.g., dibenzocyclooctyne group) that is linked to the biotin moiety. Again, this step may be done using a protocol adapted from US20110301045 or Song et al), Nat. Biotechnol. 2011 29: 68-72), for example.

The enrichment step of the method may be done using magnetic streptavidin beads, although other supports could be used. As noted above, the enriched cfDNA molecules (which correspond to the hydroxymethylated cfDNA molecules) are amplified by PCR and then sequenced.

In these embodiments, the enriched DNA sample may be amplified using one or more primers that hybridize to the added adaptors (or their complements). In embodiments in which Y-adaptors are added, the adaptor-ligated nucleic acids may be amplified by PCR using two primers: a first primer that hybridizes to the single-stranded region of the top strand of the adaptor, and a second primer that hybridizes to the complement of the single-stranded region of the bottom strand of the Y adaptor (or hairpin adaptor, after cleavage of the loop). For example, in some embodiments the Y adaptor used may have P5 and P7 arms (which sequences are compatible with Illumina's sequencing platform) and the amplification products will have the P5 sequence at one and the P7 sequence at the other. These amplification products can be hybridized to an Illumina sequencing substrate and sequenced. In another embodiment, the pair of primers used for amplification may have 3' ends that hybridize to the Y adaptor and 5' tails that either have the P5 sequence or the P7 sequence. In these embodiment, the amplification products will also have the P5 sequence at one and the P7 sequence at the other. These amplification products can be hybridized to an Illumina sequencing substrate and sequenced. This amplification step may be done by limited cycle PCR (e.g., 5-20 cycles).

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

In certain embodiments, the sample sequenced may comprise a pool of DNA molecules from a plurality of samples, wherein the nucleic acids in the sample have a molecular barcode to indicate their source. In some embodiments the nucleic acids being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

The sequence reads may be analyzed by a computer and, as such, instructions for performing the steps set forth below may be set forth as programing that may be recorded in a suitable physical computer readable storage medium.

In some embodiments, the sequence reads may be analyzed to provide a quantitative determination of which sequences are hydroxymethylated in the cfDNA. This may be done by, e.g., counting sequence reads or, alternatively, counting the number of original starting molecules, prior to amplification, based on their fragmentation breakpoint and/or whether they contain the same indexer sequence. The use of molecular barcodes in conjunction with other features of the fragments (e.g., the end sequences of the fragments, which define the breakpoints) to distinguish between the fragments is known. Molecular barcodes and exemplary methods for counting individual molecules are described in Casbon (Nucl. Acids Res. 2011, 22 e81) and Fu et al (Proc Natl Acad Sci USA. 2011 108: 9026-31), among others. Molecular barcodes are described in US 2015/0044687, US 2015/0024950, US 2014/0227705, U.S. Pat. Nos. 8,835,358 and 7,537,897, as well as a variety of other publications.

In certain embodiments, two different cfDNA samples may be compared using the above methods. The different samples may be composed of an "experimental" sample, i.e., a cfDNA sample of interest, and a "control" cfDNA sample to which the experimental cfDNA sample may be compared. In many embodiments, the different samples are obtained from subjects, one subject being a subject of interest, e.g., patient with a disease, and the other a control subject, a patient does not have the disease. Exemplary sample pairs include, for example, cfDNA from a subject having a disease such as colon, breast, prostate, lung, skin cancer, or infected with a pathogen etc.) and cfDNA from normal subjects that do not have the disease, and cfDNA from two different time points from the same subject, e.g., before and after administration of a therapy, etc.

Also provided is a method for identifying a hydroxymethylation pattern that correlates with phenotype, e.g., a disease, condition or clinical outcome, etc. In some embodiments, this method may comprise (a) performing the above-described method on a plurality of cfDNA samples, wherein the cfDNA samples are isolated from patients having a known phenotype, e.g., disease, condition or clinical outcome, thereby determining which sequences are hydroxymethylated in cfDNA from each of the patients; and (b) identifying a hydryoxymethylation signature that is correlated with the phenotype.

In some embodiments, the hydyoxymethylation signature may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective).

Also provided is a method for analyzing a patient sample. In this embodiment, the method may comprise: (a) identifying, using the above-described method, sequences that are hydroxymethylated in the cfDNA of a patient; (b) comparing the identified sequences to a set of signature sequences that are correlated with a phenotype, e.g., a disease, condition, or clinical outcome etc.; and (c) providing a report indication a correlation with phenotype. This embodiment may further comprise making a diagnosis, prognosis or theranosis based on the results of the comparison.

In some embodiments, the method may involve creating a report as described above (an electronic form of which may have been forwarded from a remote location) and forwarding the report to a doctor or other medical professional to determine whether a patient has a phenotype (e.g., cancer, etc) or to identify a suitable therapy for the patient. The report may be used as a diagnostic to determine whether the subject has a disease or condition, e.g., a cancer. In certain embodiments, the method may be used to determine the stage or type cancer, to identify metastasized cells, or to monitor a patient's response to a treatment, for example.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the report may be analyzed by an MD or other qualified medical professional, and a report based on the results of the analysis of the image may be forwarded to the patient from which the sample was obtained.

Also provided is a method for analyzing a sample comprising (a) determining, using the method described above, which sequences are hydroxymethylated in a first sample of cfDNA and which sequences are hydroxymethylated in the second sample of cfDNA, wherein the first and second samples of cfDNA are obtained from the same patient at two different time points; and (b) comparing the hydroxymethylation pattern for the first sample to the hydroxymethyation pattern for the second sample to determine if there has been a change in hydroxymethylation over time. This method may be quantitative and, in some embodiments, the comparing step (b) may comprise comparing the level of hydroxymethylation of one or more selected sequences. The comparison step of this method may map of the changes in hydroxymethylation in the course of a disease, condition, or a treatment of a disease or condition.

The phenotype of a patient can be any observable characteristic or trait of a subject, such as a disease or condition, a disease stage or condition stage, susceptibility to a disease or condition, prognosis of a disease stage or condition, a physiological state, or response to therapeutics, etc. A phenotype can result from a subject's gene expression as well as the influence of environmental factors and the interactions between the two, as well as from epigenetic modifications to nucleic acid sequences.

The phenotype in a subject can be characterized by analyzing cfDNA using the method described above. For example, characterizing a phenotype for a subject or individual may include detecting a disease or condition (including pre-symptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The products and processes described herein allow assessment of a subject on an individual basis, which can provide benefits of more efficient and economical decisions in treatment.

In some embodiments, the method may be used to identify a signature that predicts whether a subject is likely to respond to a treatment for a disease or disorder.

Characterizing a phenotype may include predicting the responder/non-responder status of the subject, wherein a responder responds to a treatment for a disease and a non-responder does not respond to the treatment. If a hydroxymethylation signature in a subject more closely aligns with that of previous subjects that were known to respond to the treatment, the subject can be characterized, or predicted, as a responder to the treatment. Similarly, if the hydroxymethylation signature in the subject more closely aligns with that of previous subjects that did not respond to the treatment, the subject can be characterized, or predicted as a non-responder to the treatment. The treatment can be for any appropriate disease, disorder or other condition. The method can be used in any disease setting where a hydroxymethylation signature that correlates with responder/non-responder status is known.

In some embodiments, the phenotype comprises a disease or condition such as those listed below. For example, the phenotype can comprise the presence of or likelihood of developing a tumor, neoplasm, or cancer. A cancer detected or assessed by products or processes described herein includes, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma.

In some embodiments, the phenotype may be a premalignant condition, such as actinic keratosis, atrophic gastritis, leukoplakia, erythroplasia, lymphomatoid granulomatosis, preleukemia, fibrosis, cervical dysplasia, uterine cervical dysplasia, xeroderma pigmentosum, Barrett's Esophagus, colorectal polyp, or other abnormal tissue growth or lesion that is likely to develop into a malignant tumor. Transformative viral infections such as HIV and HPV also present phenotypes that can be assessed according to the method.

The cancer characterized by the present method may be, without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus turmor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

In further embodiments, the cancer may be an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors;

endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilms tumor. The methods of the invention can be used to characterize these and other cancers. Thus, characterizing a phenotype can be providing a diagnosis, prognosis or theranosis of one of the cancers disclosed herein.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis.

The phenotype can also comprise a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also comprise a neurological disease, such as Multiple Sclerosis (MS), Parkinson's Disease (PD), Alzheimer's Disease (AD), schizophrenia, bipolar disorder, depression, autism, Prion Disease, Picks disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also comprise an infectious disease, such as a bacterial, viral or yeast infection. For example, the disease or condition may be Whipple's Disease, Prion Disease, cirrhosis, methicillin-resistant Staphylococcus aureus, HIV, hepatitis, syphilis, meningitis, malaria, tuberculosis, or influenza. Viral proteins, such as HIV or HCV-like particles can be assessed in a vesicle, to characterize a viral condition.

The phenotype can also comprise a perinatal or pregnancy related condition (e.g. preeclampsia or preterm birth), metabolic disease or condition, such as a metabolic disease or condition associated with iron metabolism. For example, hepcidin can be assayed in a vesicle to characterize an iron deficiency. The metabolic disease or condition can also be diabetes, inflammation, or a perinatal condition.

A correlative "signature" may be a group of 1, 2, 3, 4, 5, 6, 7, 8, 9 or 10 or more sequences that are independently either under-hydroxymethylated or over-hydroxymethylated relative to a control (e.g., "normal" cfDNA), where, collectively the identity of the sequences and, optionally, the amount of hydroxymethylation associated with those sequences, correlates with a phenotype.

The cfDNA used in the method may be from a mammal such as bovine, avian, canine, equine, feline, ovine, porcine, or primate animals (including humans and non-human primates). In some embodiments, the subject can have a pre-existing disease or condition, such as cancer. Alternatively, the subject may not have any known pre-existing condition. The subject may also be non-responsive to an existing or past treatment, such as a treatment for cancer. In some embodiments, the cfDNA may be from a pregnant female. In some embodiments, the hydroxymethylation pattern in the fetal fraction of the cfDNA may correlate with a chromosomal abnormality in the fetus (e.g., an aneuploidy). In other embodiments, one can determine the sex of the fetus from the hydroxymethylation pattern in the fetal fraction of the cfDNA and/or determine the fetal fraction of the cfDNA.

A method that comprises (a) obtaining a sample comprising circulating cell-free DNA, (b) enriching for the hydroxymethylated DNA in the sample and (c) independently quantifying the amount of nucleic acids in the enriched hydroxymethylated DNA that map to (i.e., have sequences that correspond to) each of one or more target loci (e.g., at least 1, at least 2, at least 3, at least 4, at least 5 or at least 10 target loci) is also provided. This method may further comprise: (d) determining whether one or more nucleic acid sequences in the enriched hydroxymethylated DNA are over-represented or under represented in the enriched hydroxymethylated DNA, relative to a control. The identity of the nucleic acids that are over-represented or under represented in the enriched hydroxymethylated DNA (and, in certain cases the extent to those nucleic acids are over-represented or under represented in the enriched hydroxymethylated DNA) can be use to make a diagnosis, a treatment decision or a prognosis. For example, in some cases, analysis of the enriched hydroxymethylated DNA may identify a signature that correlates with a phenotype, as discussed above. In some embodiments, the amount of nucleic acid molecules in the enriched hydroxymethylated DNA that map to each of one or more target loci (e.g., the genes/intervals listed below) may be quantified by qPCR, digital PCR, arrays, sequencing or any other quantitative method.

In some embodiments, the diagnosis, treatment decision or prognosis may be a cancer diagnosis. In these embodiments, the target loci may include one or more (e.g., at least 1, at least 2, at least 3, at least 4, at least 5, at least 10, at least 15 or at least 20, of the following gene bodies (i.e., transcribed regions of a gene): ABRACL, ADAMTS4, AGFG2, ALDH1A3, ALG10B, AMOTL1, APCDD1L-AS1, ARL6IP6, ASF1B, ATP6V0A2, AUNIP, BAGE, C2orf62, C8orf22, CALCB, CC2D1B, CCDC33, CCNL2, CLDN15, COMMD6, CPLX2, CRP, CTRC, DACH1, DAZL, DDX11L1, DHRS3, DUSP26, DUSP28, EPN3, EPPIN-WFDC6, ETAA1, FAM96A, FENDRR, FLJ16779, FLJ31813, GBX1, GLP2R, GMCL1P1, GNPDA2, GPR26, GSTP1, HMOX2, HOXC5, IGSF9B, INSC, INSL4, IRF7, KIF16B, KIF20B, LARS, LDHD, LHX5, LINC00158, LINC00304, LOC100128946, LOC100131234, LOC100132287, LOC100506963, LOC100507250, LOC100507410, LOC255411, LOC729737, MAFF, NPAS4, NRADDP, P2RX2, PAIP1, PAX1, PODXL2, POU4F3, PSMG1, PTPN2, RAG1, RBM14-RBM4, RDH11, RFPL3, RNF122, RNF223, RNF34, SAMD11, SHISA2, SIGLEC10, SLAMF7, SLC25A46, SLC25A47, SLC9A3R2, SORD, SOX18, SPATA31E1, SSR2, STXBP3, SYT11, SYT2, TCEA3, THAP7-AS1, TMEM168, TMEM65, TMX2, TPM4, TPO, TRAM1, TTC24, UBQLN4, WASH7P, ZNF284, ZNF423, ZNF444, ZNF800, ZNF850, and ZRANB2.

Figure 12A:
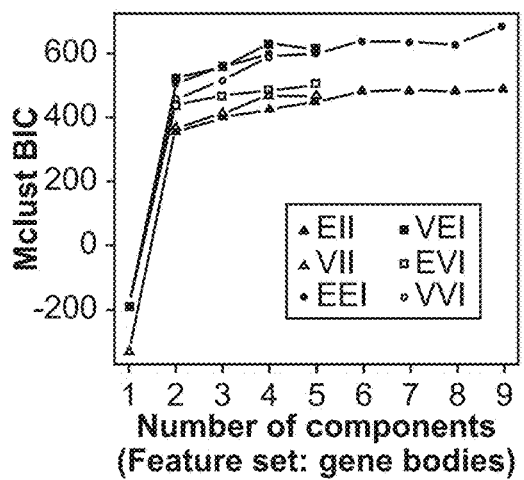
FIG. 12A-12G: Cancer type and stage prediction with cell-free 5hmC.
Figure 12B:
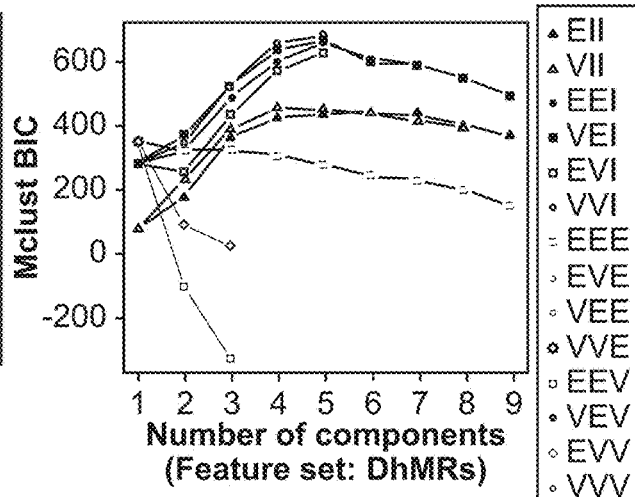
Figure 12C:
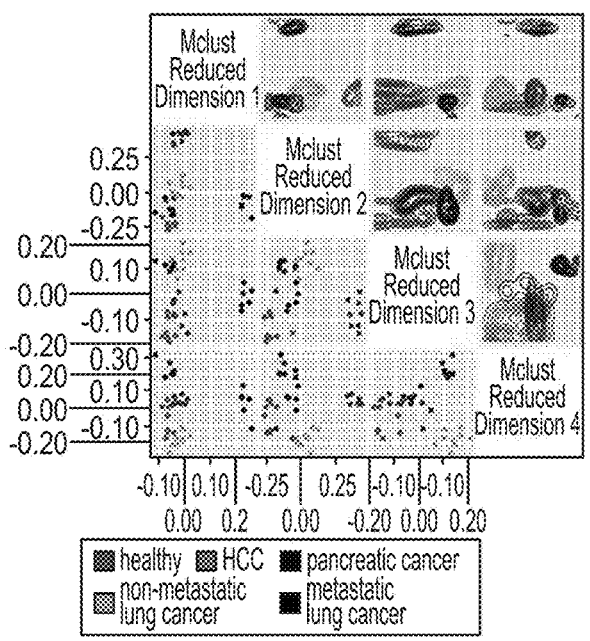
Figure 12D:
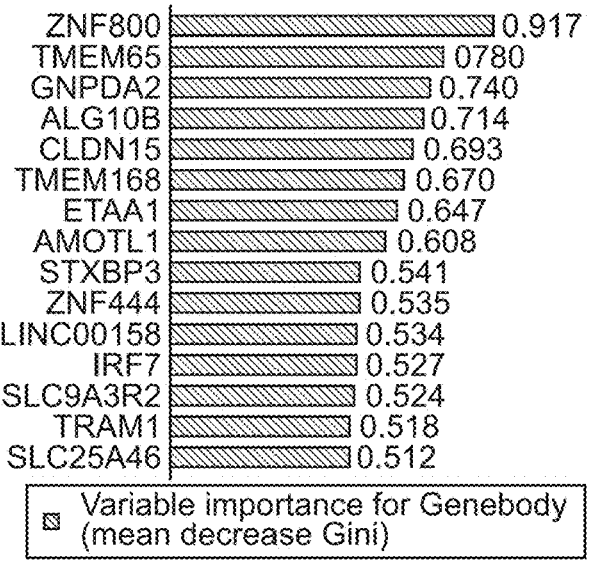

For example, in some embodiments, the amount of nucleic acids that map to each of one or more (e.g., at least 1, at least 2, at least 3, at least 4, at least 5 or at least 10) of the following gene bodies: ZNF800, TMEM65, GNPDA2, ALG10B, CLDN15, TMEM168, ETAA1, AMOTL1, STXBP3,ZNF444, LINC00158, IRF7, SLC9A3R2, TRAM1 and SLC25A46 may be independently determined, as shown in FIG. 12D.

In another example, in some embodiments, the amount of nucleic acids that map to each of one or more (e.g., at least 1, at least 2, at least 3, at least 4, at least 5 or at least 10) of the following gene bodies: CLDN15, SLC25A47, ZRANB2, LOC10050693, STXBP3, GPR26, P2RX2, LOC100507410, LHX5, HOXC5, FAM96A, CALCB, RNF223, SHISA2 and SLAMF7 may be independently determined, as shown in FIG. 12F.

In these embodiments, the target loci may include one or more (e.g., at least 1, at least 2, at least 3, at least 4, at least 5, at least 10, or at least 15) of the following intervals (where the numbering is relative to the hg19 reference genome, released as GRCh37 in February 2009): chr1:114670001-114672000, chr1:169422001-169424000, chr1:198222001-198224000, chr1:239846001-239848000, chr1:24806001-24808000, chr1:3234001-3236000, chr1:37824001-37826000, chr1:59248001-59250000, chr1:63972001-63974000, chr1:67584001-67586000, chr1:77664001-77666000, chr2:133888001-133890000, chr2:137676001-137678000, chr2:154460001-154462000, chr2:200922001-200924000, chr2:213134001-213136000, chr2:219148001-219150000, chr2:41780001-41782000, chr2:49900001-49902000, chr3:107894001-107896000, chr3:108506001-108508000, chr3:137070001-137072000, chr3:17352001-17354000, chr3:23318001-23320000, chr3:87312001-87314000, chr3:93728001-93730000, chr4:39342001-39344000, chr4:90790001-90792000, chr5:103492001-103494000, chr5:39530001-39532000, chr5:83076001-83078000, chr6:122406001-122408000, chr6:129198001-129200000, chr6:156800001-156802000, chr6:157286001-157288000, chr6:45304001-45306000, chr7:11020001-11022000, chr7:13364001-13366000, chr8:42934001-42936000, chr8:53686001-53688000, chr8:69672001-69674000, chr9:3496001-3498000 and chr9:88044001-88046000.

Figure 12E:
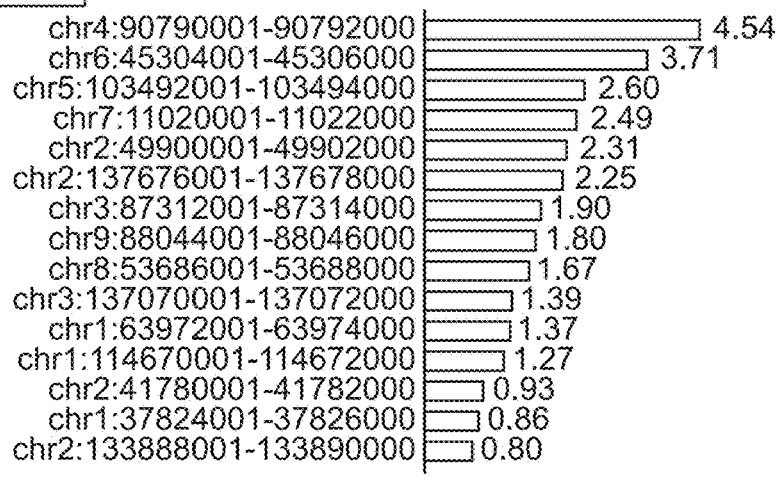
Figure 12F:
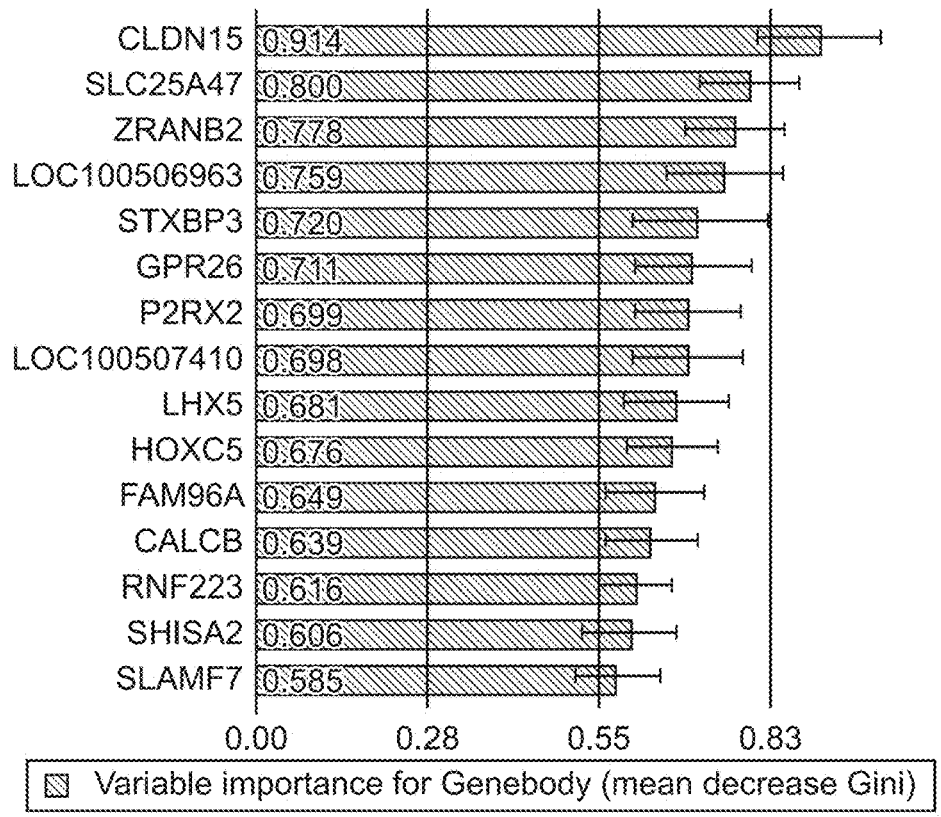

For example, in some embodiments, the amount of nucleic acids that map to each of one or more (e.g., at least 1, at least 2, at least 3, at least 4, at least 5 or all of) of the following intervals: chr4:90790001-90792000, chr6:45304001-45306000, chr5:103492001-103494000, chr7:11020001-11022000, chr2:49900001-49902000, chr2:137676001-137678000, chr3:87312001-87314000, and chr9:88044001-88046000 may be independently determined, as shown in FIG. 12E.

Figure 12G:
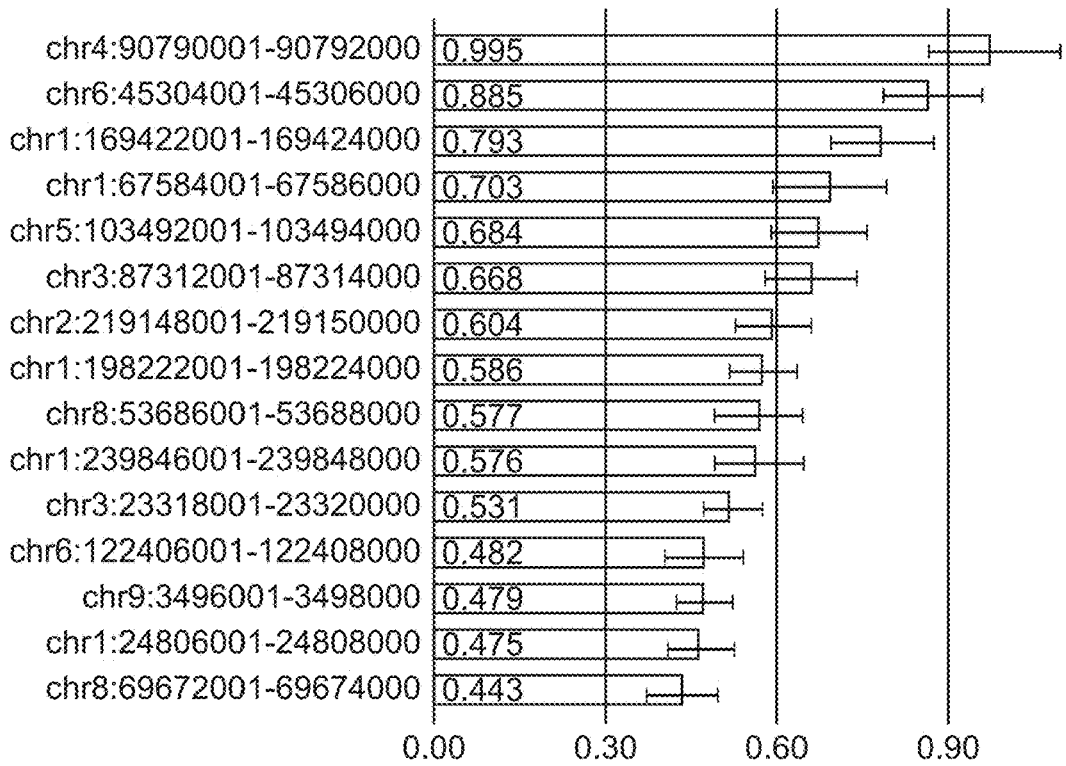
Figure 13:
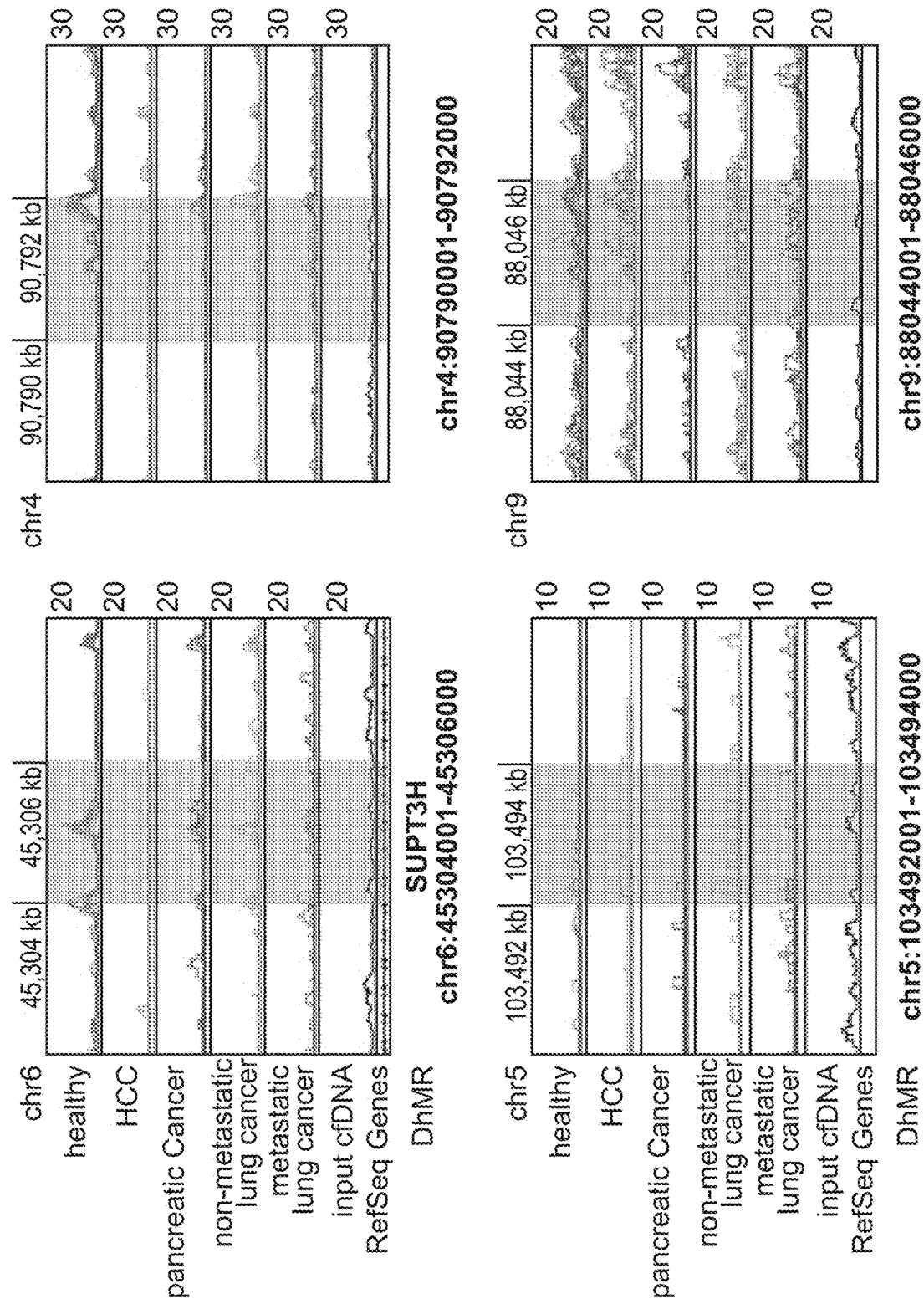
FIG. 13: Examples of DhMRs in the random forest model. Genome browser view of the cell-free 5hmC distribution in four DhMRs with high variable importance in the random forest model in various groups. Showing the overlap tracks in line plot. Shaded area indicates the DhMR.

In another example, in some embodiments, the amount of nucleic acids that map to each of one or more (e.g., at least 1, at least 2, at least 3, at least 4, at least 5 or all of) of the following intervals: chr4:90790001-90792000, chr6:45304001-45306000, chr1:169422001-169424000, chr1:67584001-67586000, chr5:103492001-103494000, chr3:87312001-87314000, chr2:219148001-219150000, chr1:198222001-198224000, chr8:53686001-53688000, chr1:239846001-239848000, chr3:23318001-23320000, chr6:122406001-122408000, chr9:3496001-3498000, chr1:24806001-24808000, and chr8:69672001-69674000, as shown in FIG. 12G.

If the diagnosis is a diagnosis of cancer, then the diagnosis may include an indication of the tissue-type of the cancer, i.e., whether the cancer is lung cancer, liver cancer, pancreatic cancer, etc.

As would be apparent, the quantification step (c) may be done using a variety of different methods. For example, as described above and below, the quantification may be done by attaching molecule identifier sequences to the enriched fragments, sequencing them, and then counting the number of molecular identifier sequences that are associated with sequences reads that map to the one or more loci (see, e.g., US20110160078). Alternatively, the quantification may be done by digital PCR (see, e.g., Kalinina et al, Nucleic Acids Research. 1997 25 (10): 1999-2004) or hybridization to an array, for example.

In some embodiments, the cfDNA sample can be additionally analyzed by the imaging method described in Song et al (Proc. Natl. Acad. Sci. 2016 113: 4338-43), which is incorporated by reference herein. In these embodiments, the method may comprise (a) labeling a sample comprising the cfDNA by: (i) adding a capture tag to the ends of the DNA molecules in the sample; and (ii) labeling molecules that comprise hydroxymethylcytosine with a first fluorophore; (b) immobilizing the DNA molecules labeled made in step (a) on a support; and (c) imaging individual molecules of hydroxymethylated DNA on the support. In some embodiments, this method may comprise (d) counting the number of individual molecules labeled with the first fluorophore, thereby determining the number of hydryoxymethylated DNA molecules in the sample. In these embodiments, the first fluorophore of step (a)(ii) is added by incubating DNA molecules with a DNA β-glucosyltransferase and UDP glucose modified with a chemoselective group, thereby covalently labeling the hydroxymethylated DNA molecules with the chemoselective group, and linking the first fluorophore to the chemoselectively-modified DNA via a cycloaddition reaction. In some embodiments, step (a)(i) may further comprises adding a second fluorophore to the ends of the DNA molecules in the sample. In some embodiments, step (a) may further comprise: after step (ii), (iii) labeling molecules that comprise methylcytosine with a second fluorophore; and step (c) further comprises imaging individual molecules of methylated DNA on the support. In these embodiments, the method may comprise (d) counting: (i) the number of individual molecules labeled with the first fluorophore and (ii) the number of individual molecules labeled with the second fluorophore. In these embodiments, the method may further comprise (e) calculating the relative amounts of hydroxymethylated DNA and methylated DNA in the sample. In some embodiments the molecules that comprise methylcytosine are labeled with the second fluorophore by: incubating the product of step (a)(ii) with a methylcytosine dioxygenase, thereby converting methylcytosine into hydroxymethylcytosine; incubating the methylcytosine dioxygenase-treated DNA with a DNA β-glucosyltransferase and UDP glucose modified with a chemoselective group, thereby covalently labeling the hydroxymethylated DNA molecules with the chemoselective group, and linking the second fluorophore to the chemoselectively-modified DNA via a cycloaddition reaction.

In this method, step (a) may further comprise: iii. labeling molecules that comprise methylcytosine with a second fluorophore; and step (c) may comprise imaging individual molecules of genomic DNA by detecting a FRET (fluorescence resonance energy transfer) signal emanating from the first or second fluorophores of (a)(ii) or (a)(iii), wherein a FRET signal indicates that a molecule has a hydroxymethylcytosine and a methylcytosine that are proximal to one another. In these embodiments, the method may comprise determining if the molecule has a proximal hydroxymethylcytosine and methylcytosine on the same strand. Alternatively or in addition, the method may comprise determining if the molecule has a proximal hydroxymethylcytosine and methylcytosine on different strands.

The hydroxymethylcytosine/methylcytosine status of the genes/intervals listed in Tables 10A, 10B, 11A and 11B can be investigated using an array of probes. For example, in some embodiments, the method may comprise attaching labels to DNA molecules that comprise one or more hydroxymethylcytosine and methylcytosine nucleotides in a cfDNA sample, wherein the hydroxymethylcytosine nucleotides are labeled with a first optically detectable label (e.g., a first fluorophore) and the methylcytosine nucleotides are labeled with a second optically detectable label (e.g., a second fluorophore) that is distinguishable from the first label, to produce a labeled sample, and hybridizing the sample with an array of probes, where the array of probes comprises probes for at least 1, at least 2, at least 3, at least 4, at least 5, at least 10 or at least 20 of the genes or intervals listed in Tables 10A, 10B, 11A and 11B. In some cases, the array may contain top strand probes and bottom strand probes, thereby allowing the labeled top and bottom strands to be detected independently.

In some embodiments, the method may comprise attaching labels to DNA molecules that comprise one or more hydroxymethylcytosine and methylcytosine nucleotides in a sample of cfDNA, wherein the hydroxymethylcytosine nucleotides are labeled with a first capture tag and the methylcytosine nucleotides are labeled with a second capture tag that is different to the first capture, to produce a labeled sample; enriching for the DNA molecules that are labeled; and sequencing the enriched DNA molecules. This embodiment of the method may comprise separately enriching the DNA molecules that comprise one or more hydroxymethylcytosines and the DNA molecules that comprise one or more methylcytosine nucleotides. The labeling may be adapted from the methods described above or from Song et al (Proc. Natl. Acad. Sci. 2016 113: 4338-43), where capture tags are used instead of fluorescent labels. For example, in some embodiments the method may comprise incubating the cfDNA (e.g., adaptor-ligated cfDNA) with a DNA β-glucosyltransferase and UDP glucose modified with a chemoselective group, thereby covalently labeling the hyroxymethylated DNA molecules in the cfDNA with the chemoselective group; linking a first capture agent to the chemoselectively-modified cfDNA via the chemoselective group, e.g., via a cycloaddition reaction; incubating this product of step with a methylcytosine dioxygenase, a DNA β-glucosyltransferase and UDP glucose modified with a chemoselective group; and linking the second capture agent to the chemoselectively-modified DNA via the chemoselective group, e.g., via a cycloaddition reaction.

In some embodiments, the determining step may be done relative to a control. Specifically, in some embodiments, the method may comprise determining whether one or more nucleic acid sequences in the enriched hydroxymethylated DNA are over-represented, relative to a control and/or determining whether one or more nucleic acid sequences in the enriched hydroxymethylated DNA are under-represented relative to a control. In some embodiments, the control sequences may be in the enriched hydroxymethylated DNA. In these embodiments, the control sequences may be in the same sample as the nucleic acids that map to the target loci, but they do not map to the target loci. In other embodiments, the control sequences may be in in the sample of (a), in the sample comprising circulating cell-free DNA, prior to enrichment for the hydroxymethylated DNA. In other embodiments, the control sequences may be in in the sample of (a), in the sample comprising circulating cell-free DNA, after enrichment for the hydroxymethylated DNA (i.e., in the fraction of circulating cell-free DNA that does not contain the hydroxymethylated DNA. In other embodiments, the control sequences can be from a different sample. In other embodiments, the determination may be based on a empirically-derived threshold obtained from analysis of multiple samples.

Kits

Also provided by this disclosure are kits that contain reagents for practicing the subject methods, as described above. The subject kits contain one or more of any of the components described above. For example, in some embodiments, the kit may be for analyzing cfDNA. In these embodiments, the kit may comprise a DNA β-glucosyltransferase, UDP glucose modified with a chemoselective group; and an adaptor comprising a molecular barcode, as described above. In some embodiments, the adaptor may be a Y or hairpin adaptor. In some embodiments, the kit may also comprise a biotin moiety, wherein the biotin moiety is reactive with the chemoselective group.

The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Compositions

Also provided by this disclosure are a variety of composition that comprise products made by the present method. In some embodiments, the composition may comprise circulating cell-free DNA, wherein the hydroxymethylcytosines residues in the DNA are modified to contain a capture tag. In these embodiments, the both strands of the circulating cell-free DNA may be in the composition. In some embodiments, the DNA may be in double-stranded form. In other embodiments, the DNA may be in single stranded form (e.g., if the composition has been denatured by incubation at an elevated temperature, for example.

As would be apparent from the description in the methods section of this disclosure, the capture tag may be a biotin moiety (e.g., biotin) or a chemoselective group (e.g., an azido group and an alkynyl group such as UDP-6-N3-Glu). In some embodiments, the composition may further comprise: i. β-glucosyltransferase and ii. UDP glucose modified with a chemoselective group (e.g., UDP-6-N3-Glu). These molecules are not fluorescently labeled, or labeled with an optically detectable label.

In some embodiments, the cell-free hydroxymethylated DNA is adaptor-ligated (i.e., has been ligated to adaptors). In some embodiments, the DNA may have adaptors, e.g., double-stranded, Y or hairpin adaptors, ligated to both strands at both ends.

In some embodiments, the composition may be an enriched composition in that at least 10% (e.g., at least 20%, at least 50%, at least 80% or at least 90%) of the nucleic acid molecules in the composition comprise one or more hydroxymethylcytosines that are modified to contain the capture tag. In these embodiments, the composition may further comprise, in solution, copies of the cell-free hydroxymethylated DNA that have been made by PCR. In these embodiments, the composition may comprise a population of PCR products, wherein at least 10% (e.g., at least 20%, at least 50%, at least 80% or at least 90%) of the PCR products are copied (directly or indirectly) from hydroxymethylated DNA.

In some embodiments, the composition may further comprise a support (e.g., a bead such as a magnetic bead or another solid), wherein the support and circulating cell-free DNA are linked to one another via the capture tag. The linkage may be via a covalent bond or a a non-covalent bond. As would be apparent, the support may be linked to streptavidin and the capture agent may be linked to biotin.

EXAMPLES

Aspects of the present teachings can be further understood in light of the following examples, which should not be construed as limiting the scope of the present teachings in any way.

Reported herein is the first global analysis of hydroxymethylome in cfDNA. In lung cancer a characteristic global loss of cell-free 5hmC was observed, while in HCC and pancreatic cancer significant finer scale changes of cell-free 5hmC were identified. In HCC, an exploratory study of the longitudinal samples was conducted, and it was demonstrated that cell-free 5hmC can be used to monitor treatment and recurrence. These three types of cancer displayed distinct patterns in their cell-free hydroxmethylome and we could employ machine learning algorithms trained with cell-free 5hmC features to predict the three cancer types with high accuracy. It is anticipated that cell-free 5hmC profiling will be a valuable tool for cancer diagnostics, as well as for other disease areas, including but not limited to neurodegenerative diseases, cardiovascular diseases and diabetes. Additionally, the general framework of this method can be readily adopted to sequence other modifications in cell-free nucleic acids by applying the appropriate labeling chemistry to the modified bases. This will allow a comprehensive and global overview of genetic and epigenetic changes of various disease states, and further increase the power of personalized diagnostics.

Figure 5A:
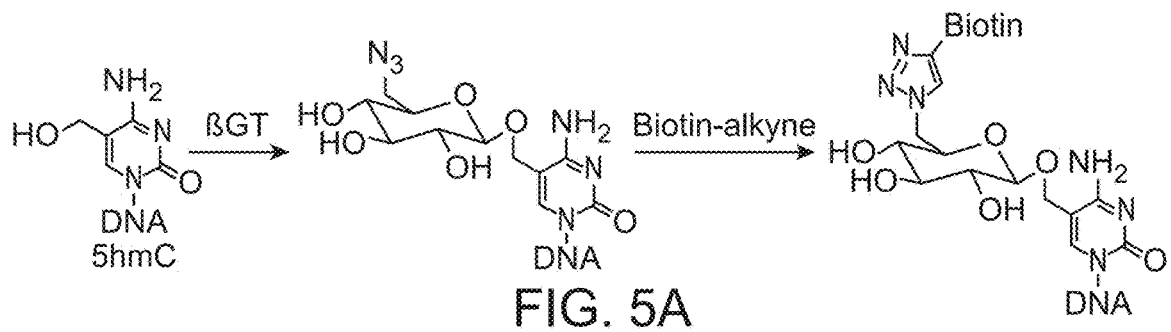
FIGS. 5A-5F: Cell-free ShmC sequencing by modified hMe-Seal.

This data was obtained using a low-input whole-genome cell-free 5hmC sequencing method adapted from a selective chemical labeling known as "hMe-Seal" (see, e.g., Song et al, Nat. Biotechnol. 2011 29, 68-72). hMe-Seal is a robust method that uses (β-glucosyltransferase (βGT) to selectively label 5hmC with a biotin via an azide-modified glucose for pull-down of 5hmC-containing DNA fragments for sequencing (See, FIG. 5A). Standard hMe-Seal procedure requires micrograms of DNA. In the modified approach described herein, cfDNA was first ligated with sequencing adapters and 5hmC was selectively labeled with a biotin group. After capturing cfDNA containing 5hmC using streptavidin beads, the final library is made by PCR directly from the beads instead of eluting the captured DNA. This minimize sample loss during purification. The method is schematically illustrated in FIG. 1A). cl Materials and Methods Sample Collection and Processing Samples for healthy subjects were obtained from Stanford blood center. HCC and breast cancer patients were recruited in a Stanford University Institutional Review Board-approved protocol. Lung cancer, pancreatic cancer, GBM, gastric cancer and colorectal cancer patients were recruited in a West China Hospital Institutional Review Board-approved protocol. All recruited subjects gave informed consent. Blood was collected into EDTA-coated Vacutainers. Plasma was collected from the blood samples after centrifugation at 1,600×g for 10 min at 4° C. and 16,000×g at 10 min at 4° C. cfDNA was extracted using the Circulating Nucleic Acid Kit (Qiagen). Whole blood genomic DNA was extracted using the DNA Mini Kit (Qiagen) and fragmented using dsDNA Fragmentase (NEB) into average 300 bp. DNA was quantified by Qubit Fluorometer (Life Technologies). Cell-free RNA was extracted using the Plasma/Serum Circulating and Exosomal RNA Purification Kit (Norgen). The extracted cell-free RNA was further digested using Baseline-ZERO DNases (Epicentre) and depleted using Ribo-Zero rRNA Removal Kit (Epicentre) according to a protocol from Clontech.

Spike-In Amplicon Preparation

To generate the spiked-in control, lambda DNA was PCR amplified by Taq DNA Polymerase (NEB) and purified by AMPure XP beads (Beckman Coulter) in nonoverlapping ~180 bp amplicons, with a cocktail of dATP/dGTP/dTTP and one of the following: dCTP, dmCTP, or 10% dhmCTP (Zymo)/90% dCTP. Primers sequences are as follows: dCTP FW-CGTTTCCGTTCTTCTTCGTC (SEQ ID NO:1), RV-TACTCGCACCGAAAATGTCA (SEQ ID NO:2), dmCTP FW-GTGGCGGGTTATGATGAACT (SEQ ID NO:3), RV-CATAAAATGCGGGGATTCAC (SEQ ID NO:4), 10% dhmCTP/90% dCTP FW-TGAAAACGAAAGGGGA-TACG (SEQ ID NO:5), RV-GTCCAGCTGGGAGTCGA-TAC (SEQ ID NO:6).

5hmC Library Construction, Labeling, Capture and High-Throughput Sequencing cfDNA (1-10 ng) or fragmented whole blood genomic DNA (1 µg) spiked with amplicons (0.001 pg of each amplicon per 10 ng DNA) was end repaired, 3'-adenylated and ligated to DNA Barcodes (Bioo Scientific) using KAPA Hyper Prep Kit (Kapa Biosystems) according to the manufacturer's instructions. Ligated DNA was incubated in a 25 µL solution containing 50 mM HEPES buffer (pH 8), 25 mM $MgCl_2$, 100 µM UDP-6-$N_3$-Glc (Active Motif), and 12.5 U βGT (Thermo) for 2 hr at 37° C. After that, 2.5 µL DBCO-PEG4-biotin (Click Chemistry Tools, 20 mM stock in DMSO) was directly added to the reaction mixture and incubated for 2 hr at 37° C. Next, 10 µg sheared salmon sperm DNA (Life Technologies) was added into the reaction mixture and the DNA was purified by Micro Bio-Spin 30 Column (Bio-Rad). The purified DNA was incubated with 0.5 µL M270 Streptavidin beads (Life Technologies) pre-blocked with salmon sperm DNA in buffer 1 (5 mM Tris pH 7.5, 0.5 mM EDTA, 1 M NaCl and 0.2% Tween 20) for 30 mM. The beads were subsequently undergone three 5-min washes each with buffer 1, buffer 2 (buffer 1 without NaCl), buffer 3 (buffer 1 with pH 9) and buffer 4 (buffer 3 without NaCl). All binding and washing were done at room temperature with gentle rotation. Beads were then resuspended in water and amplified with 14 (cfDNA) or 9 (whole blood genomic DNA) cycles of PCR amplification using Phusion DNA polymerase (NEB). The PCR products were purified using AMPure XP beads. Separate input libraries were made by direct PCR from ligated DNA without labeling and capture. For technical replicates, cfDNA from the same subject was divided into two technical replicates. Pair-end 75 bp sequencing was performed on the NextSeq instrument.

Data Processing and Gene Body Analysis

FASTQ sequences were aligned to UCSC/hg19 with Bowtie2 v2.2.5 and further filtered with samtools-0.1.19 (view-f2-F1548-q30 and rmdup) to retain unique non-duplicate matches to the genome. Pair-end reads were extended and converted into bedgraph format normalized to the total number of aligned reads using bedtools, and then converted to bigwig format using bedGraphToBigWig from the UCSC Genome Browser for visualization in Integrated Genomics Viewer. FASTQ sequences were also aligned to the three spike-in control sequences to evaluate the pull-down efficiency. The spike-in control is only used as a validation of successful pull-down in each sample. hMRs were identified with MACS using unenriched input DNA as background and default setting (p-value cutoff 1e-5). Genomic annotations of hMRs were performed by determining the percentage of hMRs overlapping each genomic regions≥1 bp. Metagene profile was generated using ngs.plot. ShmC FPKM were calculated using the fragment counts in each RefSeq gene body obtained by bedtools. For differential analyses, genes shorter than 1 kb or mapped to chromosome X and Y were excluded. Differential genic ShmC analysis was performed using the limma package in R. GO analyses were performed using DAVID Bioinformatics Resources with GOTERM_BP_FAT. Tissue-specific gene expression was obtained from BioGPS. For tSNE plot, the Pearson correlation of gene body ShmC FPKM was used as the distance matrix to tSNE. MA-plot, hierarchical clustering, tSNE, LDA, and heatmaps were done in R.

Cancer Type and Stage Prediction

Cancer type-specific marker genes were selected by performing student t-test between 1) one cancer group and healthy group, 2) one cancer group and other cancer samples, 3) two different cancer groups. Benjamini and Hochberg correction was then performed for the raw p-value and the genes were then sorted by q-value. The top 5-20 genes with smallest q-value were selected as feature set to train the classifier. To achieve higher resolution, DhMRs were identified by first breaking the reference genome (hg19) into 2 kb windows in silico and calculating 5hmC FPKM value for each of the window. Blacklisted genomic regions that tend to show artifact signal according to ENCODE were filtered before down-stream analysis. For cancer type-specific DhMRs, student t-test and Benjamini and Hochberg correction of p-values were performed for comparison between each cancer type and healthy controls. The top 2-10 DhMRs with smallest q-value were chosen for each cancer type. Random forest and Gaussian model-based Mclust classifier were performed on the dataset using previously described features (gene bodies and DhMRs). Classifiers were trained on lung cancer, pancreatic cancer, HCC and healthy samples. Parameters for random forest analysis, including random seed and mtry (number of variables randomly sampled as candidates at each split), were fine-tuned for lowest out-of-bag estimate of error using tuneRF in randomForest package in R. The top 15 features with highest variable importance were plotted. Normal mixture model analysis was performed using Mclust R package. For Mclust model-based classifier training, bayesian information criterion (BIC) plot was performed for visualization of the classification efficacy of different multivariate mixture models. By default, EEI model (diagonal, equal volume and shape) and EDDA model-type (single component for each class with the same covariance structure among classes) were chosen for Mclust classification. To strengthen the analysis, leave-one-out (LOO) cross-validation was performed for random forest and Mclust classifier with the same parameter values. For Mclust cross-validation, cvMclustDA in the Mclust R package was used.

Cell-Free RNA Library Construction and High-Throughput Sequencing

Cell-Free RNA library was prepared using ScriptSeq v2 RNA-Seq Library Preparation Kit (Epicentre) following the FFPE RNA protocol with 19 cycles of PCR amplification. The PCR products were then purified using AMPure XP beads. Pair-end 75 bp sequencing was performed on the NextSeq instrument. RNA-seq reads were first trimmed using Trimmomatic-0.33 and then aligned using tophat-2.0.14. RPKM expression values were extracted using cufflinks-2.2.1 using RefSeq gene models.

Results and Discussion

Figure 5B:
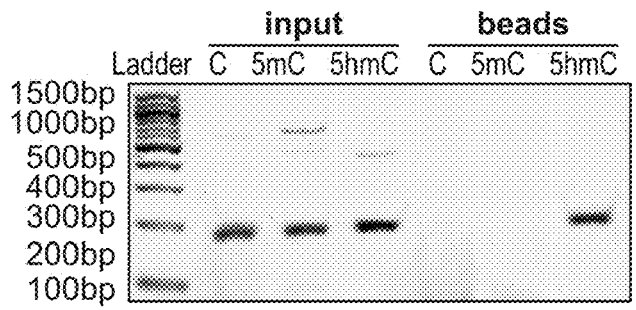
Figure 5C:
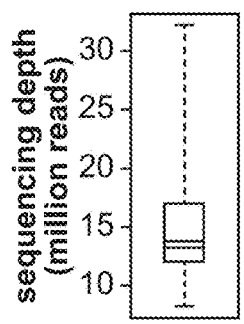

Cell-free ShmC readily from a sample that contains less than 10 ng of cfDNA (e.g., 1-10 ng of cfDNA) using the method described above. By spiking in a pool of 180 bp amplicons bearing C, SmC, or ShmC to cfDNA, it was demonstrated that only ShmC-containing DNA can be detected by PCR from the beads after pull-down (FIG. 5B). This result was confirmed in the final sequencing libraries, which showed over 100-fold enrichment in reads mapping to ShmC spike-in DNA (FIG. 1B). Furthermore, our approach performed equally well with cfDNA and bulk genomic DNA (1 µg whole blood genomic DNA (gDNA)) (FIG. 1B). The final cell-free ShmC libraries are highly complex with a median unique nonduplicate map rate of 0.75 when lightly sequenced (median 15 million reads, ~0.5-fold human genome coverage) (FIGS. 5C-5D, and Table 1 below), and yet technical replicates are highly reproducible (FIG. 1E). ShmC-enriched regions (hMRs) were identified in the sequence data using a poisson-based method. hMRs are highly concordant between technical replicates and a pooled sample: over 75% of hMRs in the pooled sample are in common with each of the replicates (FIG. 5F), reaching the ENCODE standard for ChIP-Seq. These results demonstrated cell-free ShmC can be readily and reliably profiled by the modified hMe-Seal method.

TABLE 1

Summary of 5hmC sequencing results.

| sample ID | type | total reads sequenced | unique nonduplicate mapped reads | unique nonduplicate mapped rate |
|---|---|---|---|---|
| 10 | healthy cfDNA | 20081973 | 15192613 | 0.76 |
| 11 | healthy cfDNA | 19142986 | 14762956 | 0.77 |
| 27 | healthy cfDNA | 21862078 | 16645192 | 0.76 |
| 35-1 § | healthy cfDNA | 29132339 | 16742468 | 0.57 |
| 35-2 § | healthy cfDNA | 28694218 | 17346511 | 0.60 |
| 36-1 § | healthy cfDNA | 32202519 | 20996955 | 0.65 |
| 36-2 § | healthy cfDNA | 31089686 | 20993595 | 0.68 |
| 38o | healthy cfDNA | 20124203 | 15295376 | 0.76 |
| 38 | healthy cfDNA | 20419287 | 15679281 | 0.77 |
| 39o | healthy cfDNA | 22320662 | 17833176 | 0.80 |
| input † | cfDNA input | 38574253 | 25910419 | 0.67 |
| 35-blood | whole blood gDNA | 44077590 | 31654982 | 0.72 |
| 36-blood | whole blood gDNA | 40843066 | 29266169 | 0.72 |
| blood-input † | whole blood gDNA input | 39138506 | 26455609 | 0.68 |
| lung293 | lung cancer | 14172402 | 11470840 | 0.81 |
| lung323 | lung cancer | 12269885 | 8916594 | 0.73 |
| lung324 | lung cancer | 13313728 | 10058078 | 0.76 |
| lung395 | lung cancer | 13589263 | 10092883 | 0.74 |
| lung417 | lung cancer | 13212811 | 10109574 | 0.77 |
| lung418 | lung cancer | 13103903 | 10420656 | 0.80 |
| lung419 | lung cancer | 11949356 | 9704240 | 0.81 |
| lung492 | lung cancer | 12563742 | 8885504 | 0.71 |
| lung493 | lung cancer | 12930120 | 10479700 | 0.81 |
| lung496 | lung cancer | 12267496 | 9657956 | 0.79 |
| lung512 | lung cancer | 12934833 | 10483836 | 0.81 |
| lung513 | lung cancer | 11310088 | 8304508 | 0.73 |
| lung514 | lung cancer | 12895079 | 10264145 | 0.80 |
| lung515 | lung cancer | 12132995 | 9406700 | 0.78 |
| lung517 | lung cancer | 11766082 | 8857054 | 0.75 |
| HCC150 | HCC | 15215190 | 11298385 | 0.74 |
| HCC237 | HCC | 13439935 | 10109197 | 0.75 |
| HCC241 | HCC | 16201676 | 12017320 | 0.74 |
| HCC256 | HCC | 14579945 | 10728759 | 0.74 |
| HCC260 | HCC | 13791503 | 10021911 | 0.73 |
| HCC285 | HCC | 11522024 | 7662330 | 0.67 |
| HCC290 | HCC | 13162465 | 9271065 | 0.70 |
| HCC320 | HCC | 13462633 | 9696240 | 0.72 |
| HCC341 | HCC | 11199473 | 6497400 | 0.58 |
| HCC628 | HCC | 15365745 | 11759122 | 0.77 |
| HCC324 | HCC | 12525818 | 9598812 | 0.77 |
| HCC46 | HCC | 13121530 | 9237102 | 0.70 |
| HCC73 | HCC | 13816686 | 10745247 | 0.78 |
| HCC489 | HCC | 11446887 | 5575387 | 0.49 |
| HCC195 | HCC | 11538777 | 7701351 | 0.67 |
| HCC234 | HCC | 11960087 | 8468478 | 0.71 |
| HCC626 | HCC | 13552712 | 11087605 | 0.82 |
| HCC647 | HCC | 12491614 | 8590321 | 0.69 |
| pancreatic27 | pancreatic cancer | 9717087 | 8019436 | 0.83 |
| pancreatic68 | pancreatic cancer | 10457109 | 8374219 | 0.80 |
| pancreatic69 | pancreatic cancer | 10838005 | 8940883 | 0.82 |
| pancreatic75 | pancreatic cancer | 10197772 | 8452749 | 0.83 |
| pancreatic9 | pancreatic cancer | 14601356 | 11245279 | 0.77 |
| pancreatic15 | pancreatic cancer | 15240467 | 11923009 | 0.78 |
| pancreatic22 | pancreatic cancer | 13439343 | 10356395 | 0.77 |
| GBM57 | GBM | 8799132 | 6455359 | 0.73 |
| GBM58 | GBM | 8874810 | 7253089 | 0.82 |
| GBM66 | GBM | 9795211 | 8073651 | 0.82 |
| GBM76 | GBM | 8103209 | 6165341 | 0.76 |
| stomach1 | gastric cancer | 14282633 | 10365849 | 0.73 |
| stomach2 | gastric cancer | 17825012 | 12938872 | 0.73 |
| stomach3 | gastric cancer | 16979690 | 12894400 | 0.76 |
| stomach4 | gastric cancer | 21192604 | 15675499 | 0.74 |
| stomach8 | gastric cancer | 14070772 | 8321549 | 0.59 |
| colon13 | colorectal cancer | 17352371 | 12517451 | 0.72 |
| colon16 | colorectal cancer | 15470656 | 11210513 | 0.72 |
| colon17 | colorectal cancer | 15101557 | 10590748 | 0.70 |
| colon19 | colorectal cancer | 18441208 | 12503926 | 0.68 |
| BR5-1 § | breast cancer | 17826666 | 13542700 | 0.76 |
| BR5-2 § | breast cancer | 17746176 | 13004851 | 0.73 |
| BR7-1 § | breast cancer | 16963664 | 13160842 | 0.78 |
| BR7-2 § | breast cancer | 15495003 | 12100951 | 0.78 |
| BR13 | breast cancer | 21382473 | 16015986 | 0.75 |
| BR14 | breast cancer | 18668112 | 14613260 | 0.78 |
| HBV268 | HBV | 8730571 | 5106519 | 0.58 |
| HBV334 | HBV | 11838111 | 7848078 | 0.66 |
| HBV374 | HBV | 14896634 | 11099981 | 0.75 |
| HBV397 | HBV | 12127855 | 8416798 | 0.69 |
| HBV455 | HBV | 12796382 | 9001735 | 0.70 |
| HBV640 | HBV | 10040349 | 6062886 | 0.60 |
| HBV646 | HBV | 9665264 | 5002160 | 0.52 |

§ Technical duplicate.
† Unenriched input DNA

Cell-free 5hmC was sequenced from eight healthy individuals (Tables 1 and 2). 5hmC from whole blood gDNA was also sequenced from two of the individuals, because lysed blood cells can be a major contributor to the cell-free nucleic acid. Genome-scale profiles showed that the cell-free 5hmC distributions are nearly identical between healthy individuals and are clearly distinguishable from both the whole blood 5hmC distribution and the input cfDNA (FIG. 6A). Previous studies of 5hmC in mouse and human tissues showed that the majority of 5hmC resides in the gene bodies and promoter proximal regions of the genome (Mellen et al Cell 2012 151: 1417-1430; Thomson Genome Biol. 2012 13, R93). Genome-wide analysis of hMRs in our cfDNA data showed that a majority (80%) are intragenic with most enrichment in exons (observed to expected, o/e=7.29), and depletion in intergenic regions (o/e=0.46), consistent with that in whole blood (FIGS. 6B-6C) and in other tissues. The enrichment of 5hmC in gene bodies is known to be correlated with transcriptional activity in tissues such as the brain and liver (see, e.g., Mellen et al Cell 2012 151: 1417-1430; Thomson Genome Biol. 2012 13, R93). To determine whether this relationship holds in cfDNA, we performed sequencing of the cell-free RNA from the same individual. By dividing genes into three groups according to their cell-free expression and plotting the average cell-free 5hmC profile alone gene bodies (metagene analysis), it was discovered that 5hmC is enriched in and around gene bodies of more highly expressed genes (FIG. 1C). These results supported that cell-free 5hmC is a collection from various tissue types and contains information from tissues other than the blood.

TABLE 2

Clinical information for healthy samples.

| sample ID | gender | age |
|---|---|---|
| 10 | female | 53 |
| 11 | female | 66 |
| 27 | female | 66 |
| 35 | male | 51 |
| 36 | male | 73 |
| 38o | female | 70 |
| 38 | female | 64 |
| 39o | female | 49 |

Because cell-free 5hmC were mostly enriched in the intragenic regions, genic 5hmC fragments per kilobase of gene per million mapped reads (FPKM) was used to compare the cell-free hydroxymethylome with the whole blood hydroxymethylome. Indeed, unbiased analysis of genic 5hmC using t-distributed stochastic neighbor embedding (tSNE)21 showed strong separation between the cell-free and whole blood samples (FIG. 6D). The limma package (Ritchie, et al Nucleic Acids Res. 2015: 43, e47) was used to identify 2,082 differentially hydromethylated genes between whole blood and cell-free samples (q-values (Benjamini and Hochberg adjusted p-values)<0.01, fold change>2, FIG. 7A). Notably, the 735 blood-specific 5hmC enriched genes showed increased expression in whole blood compared to the 1,347 cell-free-specific 5hmC enriched genes (p-value<$2.2 \times 10^{-16}$, Welch t-test) (FIG. 7B). In agreement with the differential expression, Gene Ontology (GO) analysis of blood-specific 5hmC enriched genes mainly identified blood cell-related processes (FIG. 7C), whereas cell-free-specific 5hmC enriched genes identified much more diverse biological processes (FIG. 7D). Examples of whole blood-specific (FPR1, FPR2) and cell-free-specific (GLP1R) 5hmC enriched genes are shown in FIG. 7E. Together, these results reinforce the concept that all tissues contribute 5hmC to cfDNA and that measurement of this is a rough proxy for gene expression.

Figure 2B:
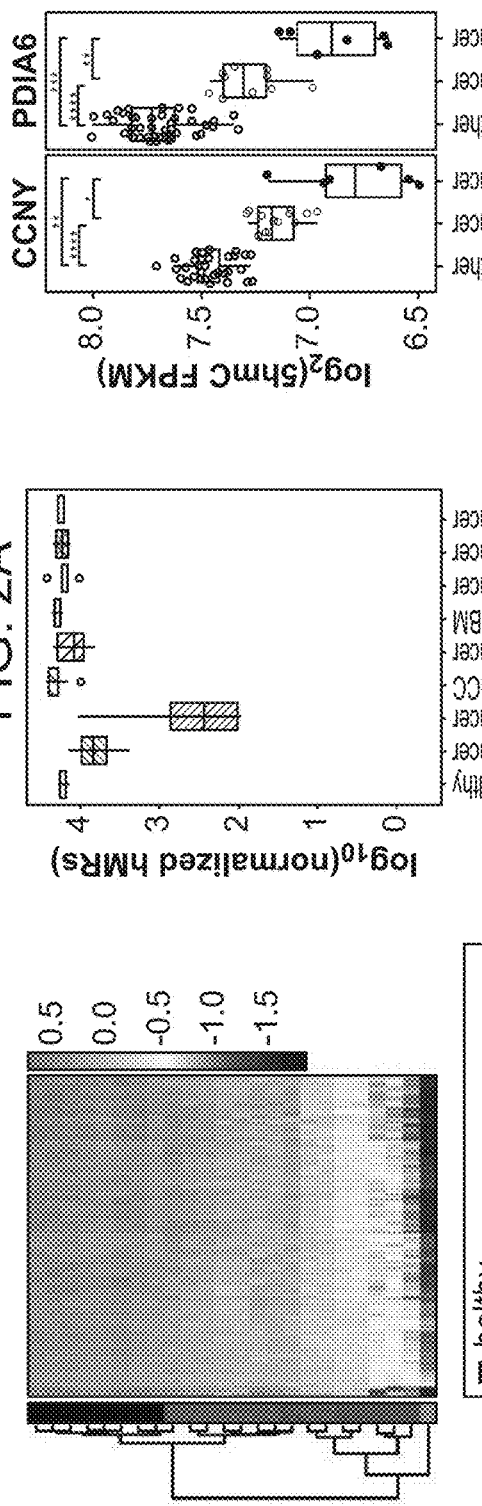
Figure 2C:
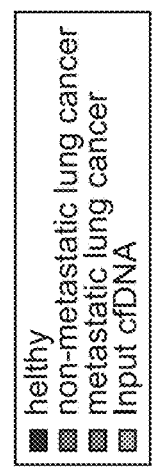

To explore the diagnostic potential of cell-free 5hmC, the method was applied to sequence cfDNA of a panel of 49 treatment-naïve primary cancer patients, including 15 lung cancer, 10 hepatocellular carcinoma (HCC), 7 pancreatic cancer, 4 glioblastoma (GBM), 5 gastric cancer, 4 colorectal cancer, 4 breast cancer patients (Table 3-9, below). These patients vary from early stage cancer to late stage metastatic cancer. In lung cancer, we observed a progressive global loss of 5hmC enrichment from early stage non-metastatic lung cancer to late stage metastatic lung cancer compared to healthy cfDNA, and it gradually resembled that of the unenriched input cfDNA (FIG. 2A). Unbiased gene body analysis using tSNE also showed a stage-dependent migration of the lung cancer profile from the healthy profile into one resembling the unenriched input cfDNA (FIG. 8A). Notably, even the early stage lung cancer samples are highly separated from the healthy samples (FIG. 8A). The global hypohydroxymethylome events were further confirmed using other metrics. First, most differential genes in metastatic lung cancer (q-values<1e-7, 1,159 genes) showed stage-dependent depletion of 5hmC compared to healthy samples (FIG. 2B). Second, the metagene profile showed a stage-dependent depletion of gene body 5hmC signal and resemblance of the unenriched input cfDNA (FIG. 8B). Third, there is a dramatic decrease in the number of hMRs identified in lung cancer, especially in metastatic lung cancer compared to healthy and other cancer samples (FIG. 2C).

These data confirmed the stage-dependent global loss of 5hmC levels in lung cancer cfDNA.

TABLE 3

Clinical information for lung cancer samples.

| sample ID | category | TNM | stage | gender | age |
|---|---|---|---|---|---|
| lung395 | non-metastatic lung cancer | T4N2Mx | III | female | 62 |
| lung419 | non-metastatic lung cancer | T1N2M0G2 | IIIa | female | 53 |
| lung492 | non-metastatic lung cancer | T2N0M0 | I | male | 55 |
| lung493 | non-metastatic lung cancer | T1N3M0 | IV | female | 66 |
| lung496 | non-metastatic lung cancer | T3N1M0 | IIIa | male | 68 |
| lung512 | non-metastatic lung cancer | — | — | female | 67 |
| lung513 | non-metastatic lung cancer | T2N1M0 | I-II | male | 47 |
| lung514 | non-metastatic lung cancer | T2N0M0 | I-II | female | 57 |
| lung515 | non-metastatic lung cancer | cT3N1M0 | IIIA | male | 52 |
| lung293 | metastatic lung cancer | cT4N3M1a | IV | female | 52 |
| lung323 | metastatic lung cancer | TxN2M1 | IV | female | 68 |
| lung324 | metastatic lung cancer | TxNxM1 | IV | male | 56 |
| lung417 § | metastatic lung cancer | — | — | male | 62 |
| lung418 | metastatic lung cancer | TxN3Mx | IIIb-IV | male | 59 |
| lung517 | metastatic lung cancer | cT4N2M1b | IV | male | 68 |

All are non-small cell lung cancer samples unless otherwise noted.
§ Small cell lung cancer.

TABLE 4

Clinical information for HCC samples.

| sample ID | category | TNM | tumor size (cm) | gender | age |
|---|---|---|---|---|---|
| HBV268 | HBV | — | — | male | 36 |
| HBV334 | HBV | — | — | female | 55 |
| HBV374 | HBV | — | — | female | 45 |
| HBV397 | HBV | — | — | female | 51 |
| HBV455 | HBV | — | — | female | 66 |
| HBV640 | HBV | — | — | female | 49 |
| HBV646 | HBV | — | — | male | 60 |
| HCC150 | HCC pre-op | pT1 pNX pMX | 3.1 § | male | 76 |
| HCC256 | HCC pre-op | pT1 pNX pMX | 15 × 9 | male | 80 |
| HCC260 | HCC pre-op | pT1 pNX pMX | 1.3 § | male | 68 |
| HCC290 | HCC pre-op | — | 10 × 13 × 18 | male | 68 |
| HCC320 | HCC pre-op | — | multifocal | female | 70 |
| HCC628 | HCC pre-op | pT1 | 1.8 § | male | 43 |
| HCC285 | HCC pre-op | pT3N0M0 | 8 § | male | 73 |
| HCC324 | HCC post-op | — | — | | 73 |
| HCC237 | HCC pre-op | pT2 pNX pMX | 4.1 § | male | 52 |
| HCC241 | HCC post-op | — | — | | 52 |
| HCC341 | HCC recurrence | — | 3 × 1.2 | | 53 |
| HCC195 | HCC pre-op | pT1 pNX pM0 | — | male | 44 |
| HCC234 | HCC pre-op | — | 1.6 § | | 44 |
| HCC626 | HCC recurrence | pT1 pNX pM0 | 1.7 × 1.7 × 1.0 | | 50 |
| HCC647 | HCC post-op | — | — | | 53 |
| HCC46 | HCC pre-op | pT2 pNX pMX | 2.8 § | male | 69 |

TABLE 4-continued

Clinical information for HCC samples.

| sample ID | category | TNM | tumor size (cm) | gender | age |
|---|---|---|---|---|---|
| HCC73 | HCC post-op | — | — | | 69 |
| HCC398 | HCC follow-up | — | — | | 72 |
| HCC489 | HCC recurrence | — | 2.2 § | | 73 |

§ in greatest dimension.

TABLE 5

Clinical information for pancreatic cancer samples.

| sample ID | TNM | stage | metastasis to | gender | age |
|---|---|---|---|---|---|
| pancreatic9 | T3N0M1 | IV | liver | male | 76 |
| pancreatic15 | T1N0M0 | IA | — | male | 64 |
| pancreatic22 | T4N1M0 | III | — | female | 71 |
| pancreatic27 | T4N1M1 | IV | abdominal wall, omentum | male | 55 |
| pancreatic68 | T3N0M1 | IV | liver | male | 63 |
| pancreatic69 | T3N0M0 | IIA | — | male | 66 |
| pancreatic75 | T3N0M0 | IIA | — | male | 54 |

TABLE 6

Clinical information for GBM samples.

| sample ID | stage | gender | age |
|---|---|---|---|
| GBM57 | IV | female | 52 |
| GBM58 | IV | male | 71 |
| GBM66 | IV | male | 81 |
| GBM76 | IV | male | 59 |

TABLE 7

Clinical information for gastric cancer samples.

| sample ID | TNM | stage | gender | age |
|---|---|---|---|---|
| stomach1 | T2N1M0 | II a | male | 67 |
| stomach2 | T4aN3bM0 | III c | male | 54 |
| stomach3 | T1aN0M0 | I a | male | 68 |
| stomach4 | T4bN0M0 | III b | male | 70 |
| stomach8 | T1bN0M0 | I a | male | 65 |

TABLE 8

Clinical information for colorectal cancer samples.

| sample ID | TNM | stage | gender | age |
|---|---|---|---|---|
| colon13 | T4N0M0 | II | male | 54 |
| colon16 | T3N0M0 | II | female | 57 |
| colon17 | T4N0M1 | IV | male | 52 |
| colon19 | PT4N1M1 | IV | female | 62 |

TABLE 9

Clinical information for breast cancer samples.

| sample ID | tumor size (cm) | tumor grade | age |
|---|---|---|---|
| BR5 | 2.5 | 2 | 54 |
| BR7 | 1.2 | 1 | 71 |

TABLE 9-continued

Clinical information for breast cancer samples.

| sample ID | tumor size (cm) | tumor grade | age |
|---|---|---|---|
| BR13 | 1 | 2 | 58 |
| BR14 | 1.9 | 1 | 61 |

Figure 2D:

It should be noted that the global loss of 5hmC enrichment seen in lung cancer cfDNA is not due to the failure of our enrichment method, as the spike-in control in all samples including the lung cancer samples showed high enrichment of 5hmC-containing DNA (FIG. 8C). It is also a phenomenon unique to lung cancer that is not observed in other cancers we tested, evidenced by the number of hMRs (FIG. 2C) and the metagene profiles (FIG. 8B). Examples of 5hmC depleted genes in lung cancer are shown in FIG. 2D and FIG. 8D. Lung cancer tissue may have a low level of 5hmC compared to normal lung tissue and lung may have a relatively large contribution to cfDNA. It is plausible that lung cancer, especially metastatic lung cancer, causes large quantities of hypohydroxymethylated gDNA to be released into cfDNA, effectively diluting the cfDNA and leading to the depletion of 5hmC in the cell-free 5hmC landscape. Alternatively or in combination, the cfDNA hypohydroxymethylation could originate from blood gDNA hypohydroxymethylation observed in metastatic lung cancer patients as recently reported. Taken together these results demonstrated that cell-free 5hmC sequencing can be used for early lung cancer detection as well as monitoring lung cancer progression and metastasis.

Figure 5D:
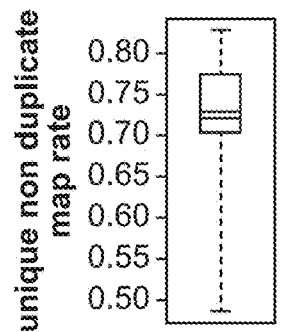
Figure 9A:
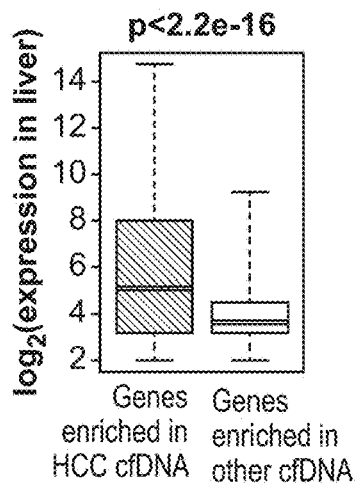
FIGS. 9A-9E: Cell-free hydroxymethylome in HCC.
Figure 9B:
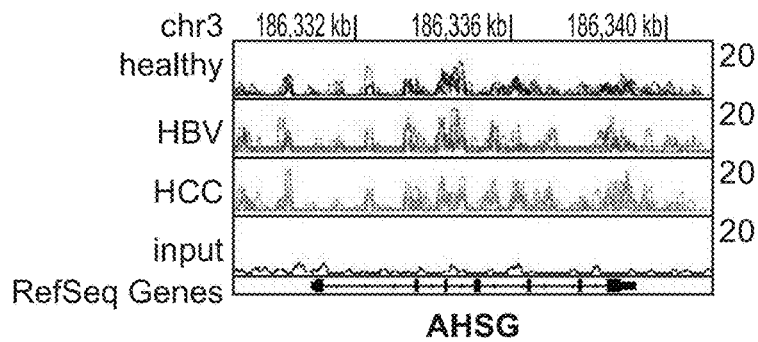
Figure 9C:
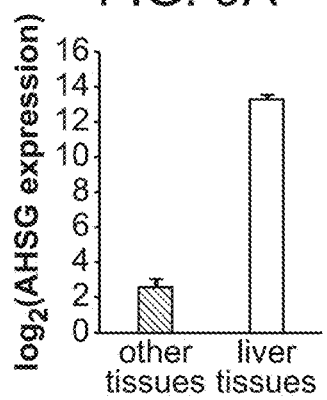
Figure 9D:
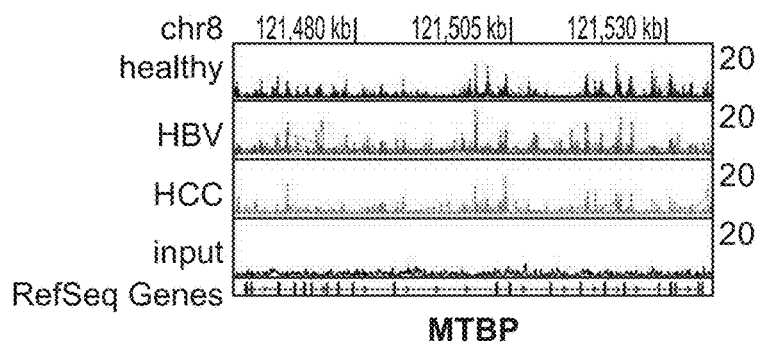
Figure 9E:
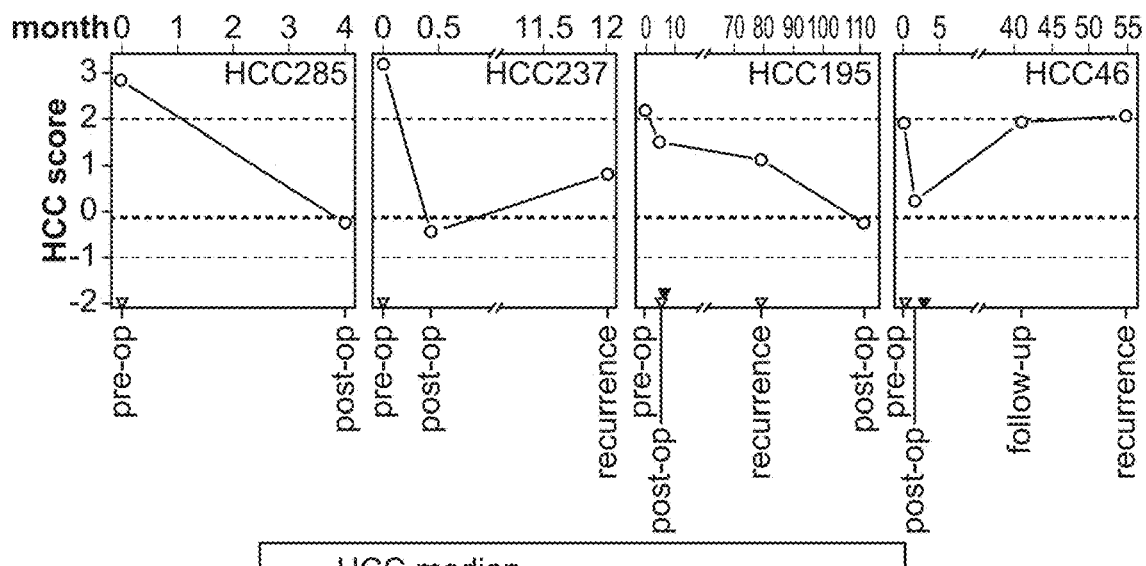

For HCC, cell-free 5hmC from seven patients with hepatitis B (HBV) infection was sequence, because most HCC cases are secondary to viral hepatitis infections (Table 4). Unbiased gene level analysis by tSNE revealed that there is a gradual change of cell-free 5hmC from healthy to HBV and then to HCC, mirroring the disease development (FIG. 3A). HCC-specific differential genes (q-values<0.001, fold change>1.41, 1,006 genes) could separate HCC from healthy and most of the HBV samples (FIG. 3B). Both HCC-specific enriched and depleted genes can be identified compared to other cfDNA samples (FIG. 3B), and the enriched genes (379 genes) showed increased expression in liver tissue compared to the depleted genes (637 genes) (p-values<$2.2\times10^{-16}$, Welch t-test) (FIG. 9A), consistent with the permissive effect of 5hmC on gene expression. An example of HCC-specific 5hmC enriched genes is AHSG, a secreted protein highly expressed in the liver (FIG. 3C and FIGS. 9B-9C), and an example of HCC-specific 5hmC depleted genes is MTBP, which was reported to inhibit migration and metastasis of HCC and was downregulated in HCC tissues (FIG. 3d and Extended Data FIG. 5d). Together, these results point to a model where virus infection and HCC development lead to a gradual damage of liver tissue and increased presentation of liver DNA in the blood.

Figure 5E:
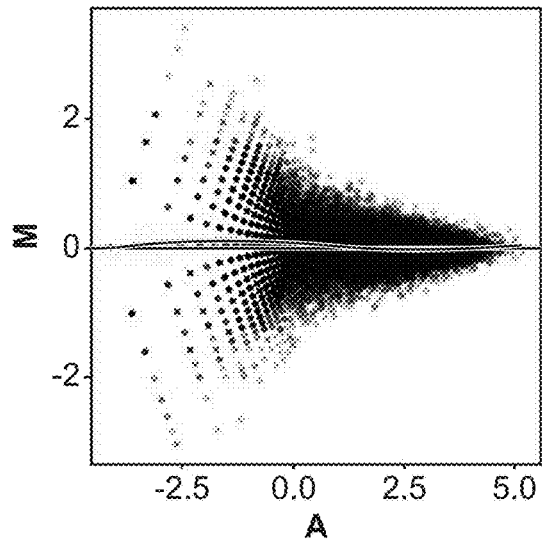
Figure 5F:
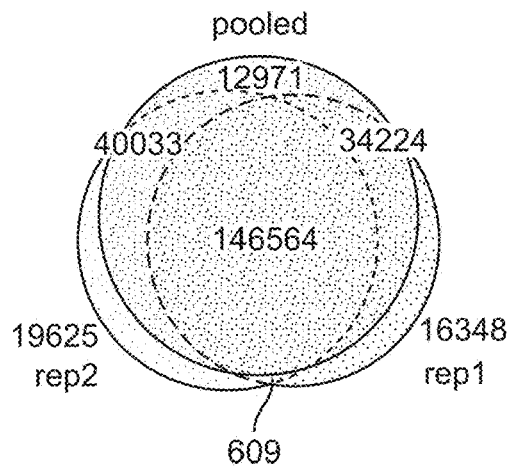

To further explore the potential of cell-free 5hmC for monitoring treatment and disease progression, four of the HCC patients were followed. These patients underwent surgical resection, out of which three of them had recurrent disease (Table 4). Analysis of serial plasma samples from these patients (pre-operation/pre-op; post-operation/post-op; and recurrence) with tSNE revealed that post-op samples clustered with healthy samples, whereas the recurrence samples clustered with HCC (FIG. 3E). This pattern was also reflected by changes in the 5hmC FPKM of AHSG and MTBP (FIGS. 3C-3D). As an example of using cell-free 5hmC for tracking HCC treatment and progression, we employed linear discriminant analysis (LDA) to define a linear combination of the HCC-specific differential genes (FIG. 3B) into to a single value (the HCC score) that best separated the pre-op HCC samples from the healthy and HBV samples. We then calculated the HCC score for the post-op and recurrence HCC samples, and showed that the HCC score can accurately track the treatment and recurrence states (FIG. 5E). Together, these results demonstrate that cell-free 5hmC sequencing is a powerful tool to detect HCC, as well as monitor treatment outcome and disease recurrence.

Figure 11B:
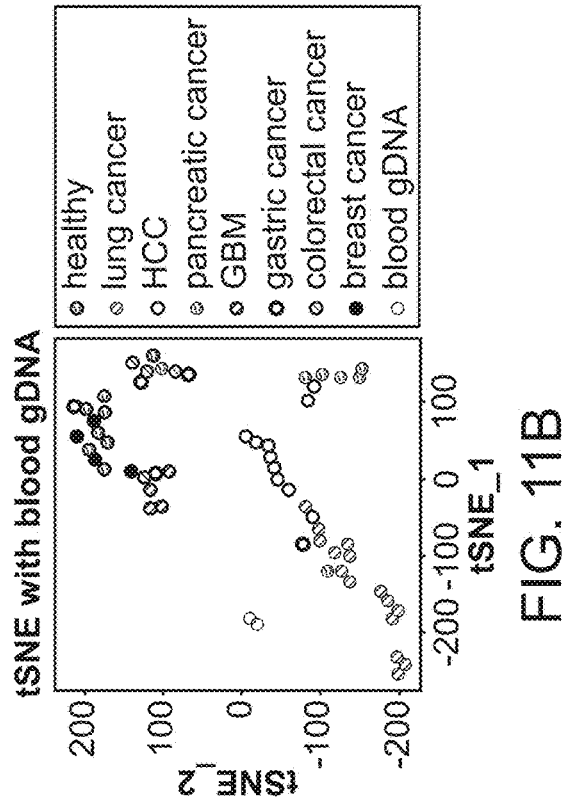
FIGS. 11A-11D: Cell-free hydroxymethylome in cancer samples.
Figure 11A:
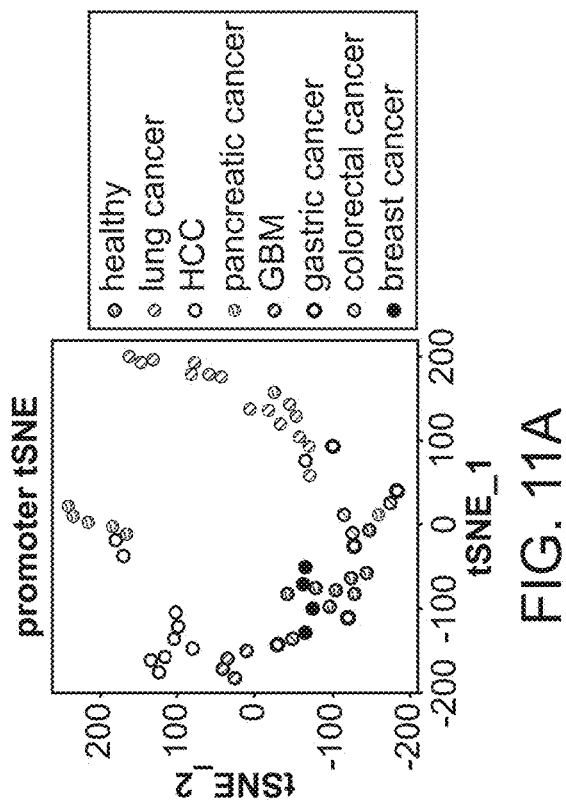
Figure 11D:
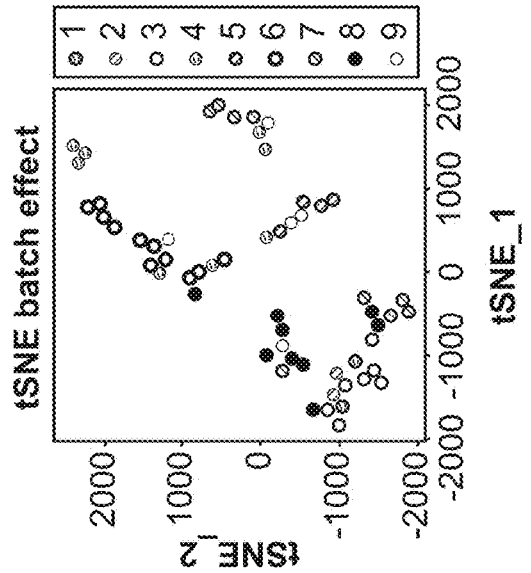
Figure 11C:
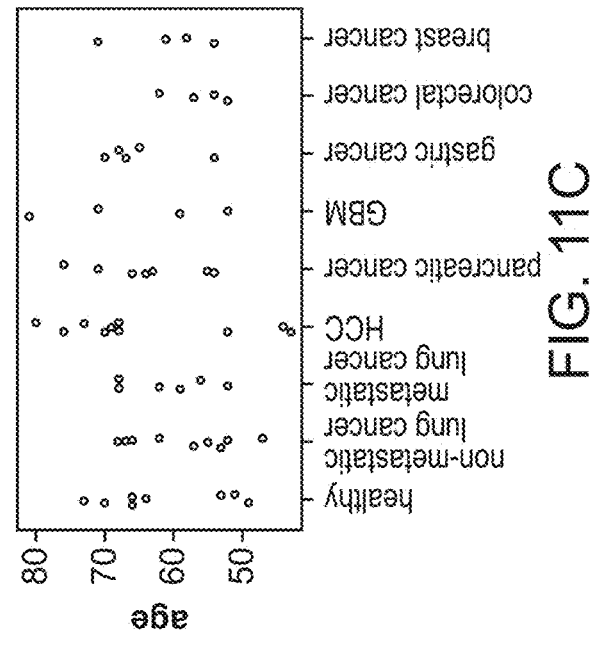

It was also found that pancreatic cancer produces drastic changes in its cell-free hydroxymethylome, even in some early stage pancreatic cancer patients (Table 5). Like HCC, pancreatic cancer lead to both upregulated and downregulated 5hmC genes compared to healthy individuals (q-value<0.01, fold change>2, 713 genes) (FIG. 10A). Examples of pancreatic cancer-specific 5hmC enriched and depleted genes compared other cfDNA samples are shown in FIGS. 6B-6E. Our results suggest that cell-free 5hmC sequencing can be potentially valuable for early detection of pancreatic cancer.

the transcription start site (TSS)) showed similar patterns (FIG. 11A). It is noted that no particular cancer type that was tested resembled the whole blood profile (FIG. 11B), suggesting that the blood cell contamination is not a significant source of variation. All patients in the panel fall in the same age range as the healthy individuals (FIG. 11C, and Tables 2-9), therefore age is unlikely to be a confounding factor. No batch effect was observed (FIG. 11D).

To further demonstrate the power of cfDNA 5hmC as a biomarkers to predict cancer types two widely used machine learning methods, the Normal mixture model and Random Forest, were employed. The prediction was focused on HCC, pancreatic cancer, non-metastatic and metastatic lung cancer. Based on three rules (see below), identified 90 genes (Table 10) were identified whose average gene body 5hmC levels could either distinguish cancer groups from healthy groups or between cancer groups.

TABLE 10A 90 gene body feature set used for cancer prediction.

| | | | | | |
|---|---|---|---|---|---|
| ASF1B | GLP2R | C2orf62 | SPATA31E1 | SLAMF7 | INSC |
| LINC00304 | LOC100507410 | DUSP26 | IRF7 | RNF34 | AUNIP |
| TTC24 | ADAMTS4 | TPM4 | DUSP28 | RNF122 | SLC9A3R2 |
| LOC255411 | ATP6V0A2 | SYT2 | COMMD6 | POU4F3 | SYT11 |
| RFPL3 | KIF16B | SHISA2 | EPPIN-WFDC6 | CPLX2 | SIGLEC10 |
| FLJ31813 | RAG1 | SLC25A46 | FLJ16779 | ZNF284 | GBX1 |
| PAIP1 | PTPN2 | APCDD1L-AS1 | SOX18 | ZNF850 | C8orf22 |
| ZNF800 | TMEM168 | GMCL1P1 | CLDN15 | RDH11 | ZNF423 |
| PODXL2 | ABRACL | LOC100507250 | NRADDP | BAGE | EPN3 |
| THAP7-AS1 | GSTP1 | CTRC | TRAM1 | ALDH1A3 | PSMG1 |
| MAFF | AMOTL1 | IGSF9B | CC2D1B | HOXC5 | LHX5 |
| FENDRR | LOC100128946 | PAX1 | TPO | CRP | LOC100131234 |
| KIF20B | NPAS4 | STXBP3 | ARL6IP6 | TMEM65 | ETAA1 |
| GNPDA2 | ALG10B | DAZL | LINC00158 | TMX2 | RBM14-RBM4 |
| SORD | HMOX2 | LDHD | ZNF444 | AGFG2 | DHRS3 |

In a second analysis using a different method, the gene bodies listed in Table 10B were identified as being predictive for cancer.

TABLE 10B

Top gene body feature set used for cancer prediction

| | | | | | |
|---|---|---|---|---|---|
| CLDN15 | SLC25A47 | ZRANB2 | LOC100506963 | STXBP3 | GPR26 |
| P2RX2 | LOC100507410 | LHX5 | HOXC5 | FAM96A | CALCB |
| RNF223 | SHISA2 | SLAMF7 | PAX1 | DACH1 | LOC100128946 |
| ASF1B | KIF16B | SSR2 | LARS | DHRS3 | CCDC33 |
| GMCL1P1 | COMMD6 | SPATA31E1 | ABRACL | SAMD11 | UBQLN4 |
| TCEA3 | SYT2 | INSL4 | RAG1 | CCNL2 | CRP |
| DDX11L1 | LOC729737 | WASH7P | LOC100132287 | | |

Figures 4A, 4B, 4C:
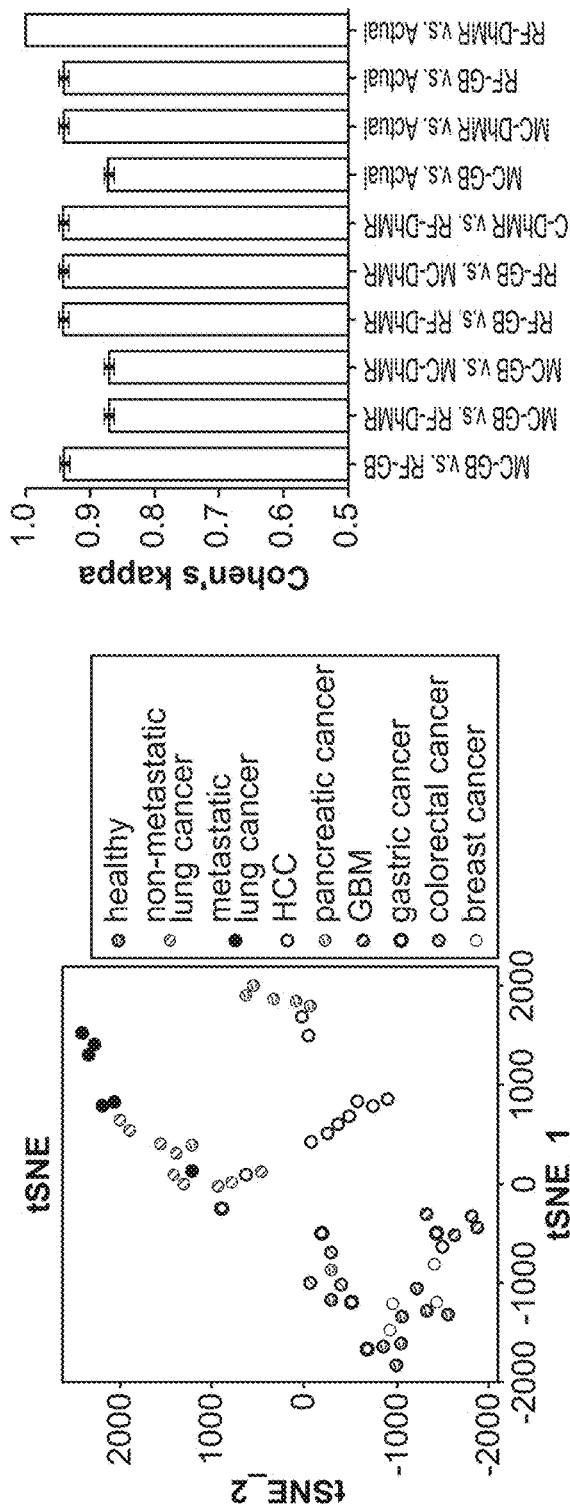
FIGS. 4A-4C: Cancer type and stage prediction with cell-free ShmC.

Although there has been great interest in using cfDNA as a "liquid biopsy" for cancer detection, it has been challenging to identify the origin of tumor cfDNA and hence the location of the tumor. Our results that analysis of cell-free 5hmC could solve this problem because tSNE analysis of all seven cancer types shows that that lung cancer, HCC, and pancreatic cancer showed distinct signatures and could be readily separated from each other and healthy samples (FIG. 4A). The other four types of cancer displayed relatively minor changes compared to the healthy samples. Using other features such as the promotor region (5 kb upstream of The target loci analyzed in the method described above may include one or more (e.g., 1, 2, 3, 4, 5, 6, 7, 8, 9, 10 or more, e.g., 15 or more or 20 or more of the gene bodies listed in Tables 10A and/or 10B, as shown above.

In addition to gene body, the 5hmC on non-coding regions could potentially serve as biomarkers in predicting cancer types. Another set of features was designed by investigating each of the 2 kb windows of the entire genome and identified differential hMRs (DhMRs) for each cancer type. 17 marker DhMRs were identified for the four distinctive cancer groups (Table 11A).

TABLE 11A

17 DhMR feature set used for cancer prediction

| | | |
|---|---|---|
| chr9: 88044001-88046000 | chr1: 63972001-63974000 | chr1: 114670001-114672000 |
| chr2: 133888001-133890000 | chr1: 37824001-37826000 | chr8: 53686001-53688000 |
| chr2: 49900001-49902000 | chr5: 103492001-103494000 | chr2: 137676001-137678000 |
| chr2: 200922001-200924000 | chr2: 41780001-41782000 | chr3: 137070001-137072000 |
| chr7: 11020001-11022000 | chr4: 90790001-90792000 | chr3: 93728001-93730000 |
| chr3: 87312001-87314000 | chr6: 45304001-45306000 | |

In a second analysis using a different method, the gene bodies listed in Table 10B were identified as being predictive for cancer.

TABLE 11B

Top DhMR feature set used for cancer prediction

| | | |
|---|---|---|
| chr4: 90790001-90792000 | chr6: 45304001-45306000 | chr1: 169422001-169424000 |
| chr1: 67584001-67586000 | chr5: 103492001 -103494000 | chr3: 87312001-87314000 |
| chr2: 219148001-219150000 | chr1: 198222001-198224000 | chr8: 53686001-53688000 |
| chr1: 239846001-239848000 | chr3: 23318001-23320000 | chr6: 122406001-122408000 |
| chr9: 3496001-3498000 | chr1: 24806001-24808000 | chr8: 69672001-69674000 |
| chr2: 49900001-49902000 | chr3: 107894001-107896000 | chr8: 42934001-42936000 |
| chr3: 17352001-17354000 | chr6: 157286001-157288000 | chr3: 108506001-108508000 |
| chr4: 39342001-39344000 | chr6: 129198001-129200000 | chr3: 137070001-137072000 |
| chr1: 59248001-59250000 | chr5: 83076001-83078000 | chr3: 93728001-93730000 |
| chr2: 213134001-213136000 | chr5: 39530001-39532000 | chr1: 3234001-3236000 |
| chr1: 37824001-37826000 | chr6: 156800001-156802000 | chr7: 13364001-13366000 |
| chr1: 77664001-77666000 | chr2: 154460001-154462000 | chr2: 41780001-41782000 |

The target loci analyzed in the method described above may include one or more (e.g., 1, 2, 3, 4, 5, 6, 7, 8, 9, 10 or more, e.g., 15 or more or 20 or more of the gene bodies listed in Tables 11A and/or 11B, as shown above.

The two machine learning algorithms were trained using either 90 genes or 17 DhMRs as features and the prediction accuracy was evaluated with leave-one-out (LOO) cross-validation. The Normal mixture model based predictor (Mclust) had LOO cross-validation error rates of 10% and 5%, when using gene body and DhMRs as features, respectively (FIG. 4B and FIGS. 12A-12B). Mclust-based dimensional reduction showed clear boundaries between the groups (FIG. 12C). The Random Forest predictor achieved LOO cross-validation error rates of 5% and 0%, when using gene body and DhMRs as features, respectively (FIG. 4B). Distinct 5hmC profiles in different cancer types of several DhMRs with high variable importance to random forest prediction model could be observed (FIGS. 12D-12E). Finally, Cohen's kappa was used to evaluate the concordance rate between different prediction models. All combinations showed high agreement (Cohen's kappa ~0.9) in inter-classifier comparison and when comparing with the actual classification (FIG. 4C). FIGS. 12F and 12G show the variable importance for gene bodies and DhMRS, obtained using a different method. These results demonstrate that cell-free 5hmC can be used for cancer diagnostics and staging.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. cfDNA analysis) those skilled in the art will recognize that its usefulness is not limited thereto and that the present invention can be beneficially utilized in any number of environments and implementations where it is desirable to examine hydroxymethylation. Accordingly, the claims set forth below should be construed in view of the full breadth and spirit of the invention as disclosed herein.

What is claimed is:

1. A method for sequencing hydroxymethylated cell-free DNA (cfDNA), comprising:
   (a) adding adaptor sequences onto the ends of cfDNA, wherein the cfDNA is not pre-digested by a restriction enzyme;
   (b) incubating the adaptor-ligated cfDNA with a DNA β-glucosyltransferase and UDP glucose modified with a chemoselective group, thereby covalently labeling the hydroxymethylated DNA molecules in the cfDNA with the chemoselective group;
   (c) linking a biotin moiety to the chemoselectively-modified cfDNA via a cycloaddition reaction;
   (d) enriching for the biotinylated DNA molecules by binding the product of step (c) to a support that binds to biotin, wherein the enriching is done without pre-amplifying the cfDNA;
   (e) amplifying the enriched DNA using primers that bind to the adaptors, wherein the amplifying is done by washing the support and setting up an amplification reaction containing the support, without releasing the enriched DNA molecules from the support; and
   (f) sequencing the amplified DNA to produce a plurality of sequence reads.

2. The method of claim 1, wherein the UDP glucose modified with a chemoselective group comprises UDP-6-$N_3$-Glu, the biotin moiety comprises dibenzocyclooctyne-modified biotin, and the support comprises avidin or streptavidin.

3. The method of claim 1, wherein the adaptor sequences comprise a molecular barcode.

4. The method of claim 3, wherein the molecular barcode comprises a sample identifier sequence and a molecule identifier sequence.

5. The method of claim 1, wherein prior to step (a), a spike-in control composition is combined with sample.

6. The method of claim 5, wherein the spike-in control composition comprises three amplicons synthesized from a cocktail of dATP, dGTP, dTTP, and (1) dCTP, (2) dmCTP, or (3) dhmCTP and dCTP.

7. A method for identifying sources of DNA in a cell-free DNA sample, comprising:
   (a) providing a sample that comprises a pool of unamplified adaptor-ligated, cell-free DNA molecules that (i) have a molecular barcode to indicate their source, (ii) are hydroxymethylated, and (iii) linked to a support via a capture tag, wherein the cfDNA is not pre-digested by a restriction enzyme;
   (b) amplifying the cell-free DNA molecules by washing the support and setting up an amplification reaction containing the support, without releasing the captured cell-free DNA from the support, to provide amplification products;
   (c) sequencing the amplification products to produce a plurality of sequence reads; and
   (d) identifying the sources of the cell-free DNA molecules from the molecular barcodes observed in the sequence reads.

8. The method of claim 7, wherein the capture tag comprises a biotin moiety.

9. The method of claim 7, wherein the sample is enriched in DNA molecules comprising one or more hydroxymethylcytosines that are modified to contain the capture tag, such that the sample comprises an enriched composition.

10. The method of claim 9, wherein at least 80% of the DNA molecules in the enriched composition comprise one or more hydroxymethylcytosines that are modified to contain the capture tag.

11. The method of claim 10, wherein at least 90% of the DNA molecules in the enriched composition comprise one or more hydroxymethylcytosines that are modified to contain the capture tag.

* * * * *